(12) United States Patent
Kim et al.

(10) Patent No.: US 10,561,688 B2
(45) Date of Patent: Feb. 18, 2020

(54) METHOD FOR PREPARING OF ENDOTHELIAL CELLS BY TRANSFORMATION (TRANSDIFFERENTIATION) OF ADULT FIBROBLAST, AND USE THEREOF

(71) Applicant: SEOUL NATIONAL UNIVERSITY R&DB FOUNDATION, Seoul (KR)

(72) Inventors: Hyo-Soo Kim, Seoul (KR); Jung-Kyu Han, Anyang-si (KR); Sung-Hwan Chang, Seoul (KR); Hyun-Ju Cho, Seoul (KR); Saet-Byeol Choi, Gyeongsangbuk-do (KR); Youngchul Shin, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 639 days.

(21) Appl. No.: 15/153,875

(22) Filed: May 13, 2016

(65) Prior Publication Data
US 2016/0250263 A1 Sep. 1, 2016

Related U.S. Application Data

(63) Continuation-in-part of application No. PCT/KR2014/010740, filed on Nov. 10, 2014.

(30) Foreign Application Priority Data

Nov. 14, 2013 (KR) ........................ 10-2013-0138570

(51) Int. Cl.
*A61K 35/44* (2015.01)
*C12N 5/071* (2010.01)
*C12N 5/16* (2006.01)
*C12N 5/077* (2010.01)

(52) U.S. Cl.
CPC .............. *A61K 35/44* (2013.01); *C12N 5/069* (2013.01); *C12N 5/0656* (2013.01); *C12N 5/16* (2013.01); *C12N 2501/60* (2013.01); *C12N 2506/1307* (2013.01); *C12N 2510/00* (2013.01)

(58) Field of Classification Search
CPC ........ A61K 35/44; C12N 5/16; C12N 5/0656; C12N 5/069; C12N 2501/60; C12N 2510/00; C12N 2506/1307; C12N 2501/998
USPC ...... 424/93.21; 435/325, 357, 366, 455, 377
See application file for complete search history.

(56) References Cited

FOREIGN PATENT DOCUMENTS

| CN | 103290051 A | 9/2013 |
|----|-------------|--------|
| JP | 2006-502094 A | 1/2006 |
| WO | 03/080798 A2 | 10/2003 |
| WO | 2009/070683 A1 | 6/2009 |

OTHER PUBLICATIONS

Ginsberg et al. (2012) Cell, vol. 151, 559-575.*
Graf et al. (2009) Nature, vol. 462(3) 587-594.*
Brooks, "Role of Integrins in Angiogenesis", Eur. J. Cancer, vol. 32A, No. 14, pp. 2423-2429, (1996).
Bussolino et al., "Molecular mechanisms of blood vessel formation", Trends Biochem. Sci., vol. 22, pp. 251-256, (1997).
De Val et al., "Transcriptional Control of Endothelial Cell Development", Developmental Cell, vol. 16, pp. 180-195, (2009).
Folkman et al., "Angiogenesis", J. Biol. Chem., vol. 267, No. 16, pp. 10931-10934, (1992).
Folkman, "Angiogenesis in cancer, vascular, rheumatoid and other disease", J. Nat. Med., vol. 1, pp. 27-31, (1995).
Ginsberg et al., "Efficient Direct Reprogramming of Mature Amniotic Cells into Endothelial Cells by ETS Factors and TGFβ Suppression", Cell, vol. 151, pp. 559-575, (2012).
Hanahan et al., "Patterns and Emerging Mechanisms of the Angiogenic Switch during Tumorigenesis", Cell, vol. 86, pp. 353-364, (1996).
Jackson et al., "The codependence of angiogenesis and chronic inflammation", FASEB J., vol. 11, pp. 457-465, (1997).
Levenberg et al., "Engineering vascularized skeletal muscle tissue", Nature Biotechnology, vol. 27, No. 7, pp. 879-884, (2005).
Park et al., "Foxo1 is essential for in vitro vascular formation from embryonic stem cells", Biochemical and Biophysical Research Communications, vol. 390, pp. 861-866, (2009).
Risau, "Mechanisms of angiogenesis", Nature, vol. 386, pp. 671-674, (1997).
Sumanas et al., "Interplay among Etsrp/ER71, Scl, and Alk8 signaling controls endothelial and myeloid cell formation", Blood, vol. 111, No. 9, pp. 4500-4510, (2008).
Wu et al., "KLF2 Transcription Factor Modulates Blood Vessel Maturation through Smooth Muscle Cell Migration", The Journal of Biological Chemistry, vol. 283, No. 7, pp. 3942-3950, (2008).

* cited by examiner

*Primary Examiner* — Anne Marie S Wehbe
(74) *Attorney, Agent, or Firm* — Vorys, Sater, Seymour & Pease LLP; Mih Suhn Koh

(57) ABSTRACT

The present invention relates to a method of preparing vascular endothelial cells by transforming (transdifferentiating) adult fibroblasts and a composition, which includes vascular endothelial cells prepared according to the method, for preventing and treating ischemic diseases, the method including a step of transducing adult fibroblasts with a gene. In particular, the present invention confirms that five factors, Foxo1, Er71, Klf2, Tal1, and Lmo2, induce transdifferentiation of adult fibroblasts into induced vascular endothelial cells. Furthermore, the present invention confirms that three factors, Er71, Klf2, and Tal1 induce transdifferentiation of human adult fibroblasts into induced vascular endothelial cells. The resultant induced endothelial cells enable lower limb salvaging by angiogenesis in lower limb ischemic animal models, showing that the induced endothelial cells can be effectively used for prevention or treatment of ischemic diseases.

7 Claims, 35 Drawing Sheets

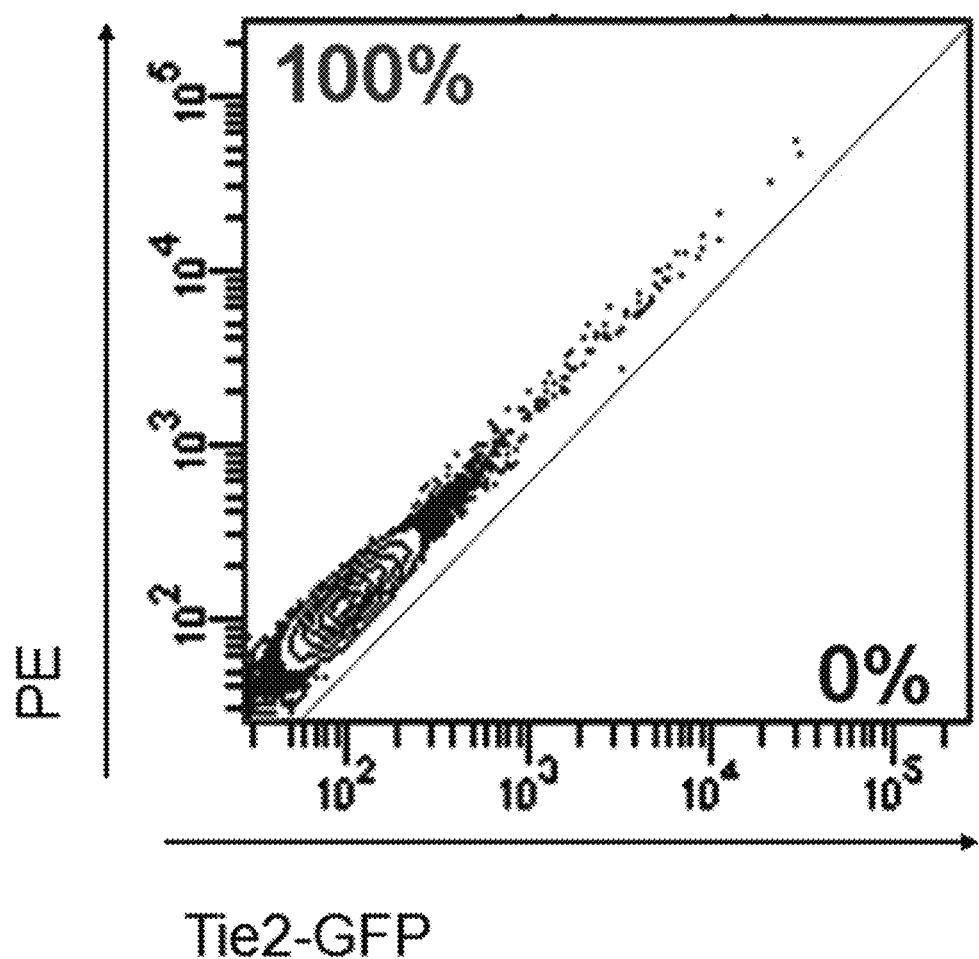
[Fig. 1]

[Fig. 2]
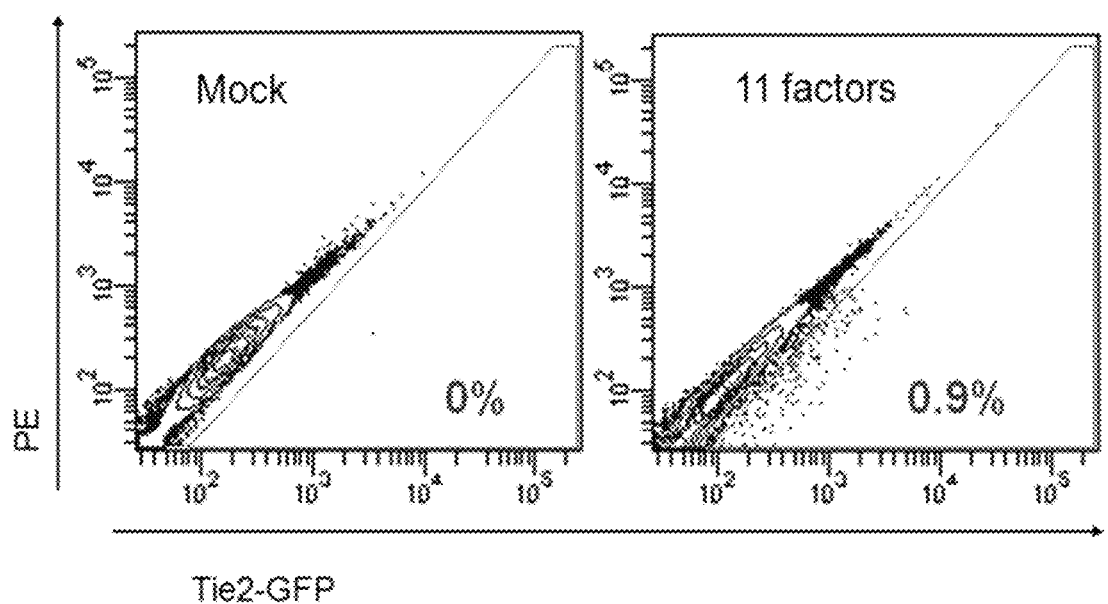

[Fig. 3]
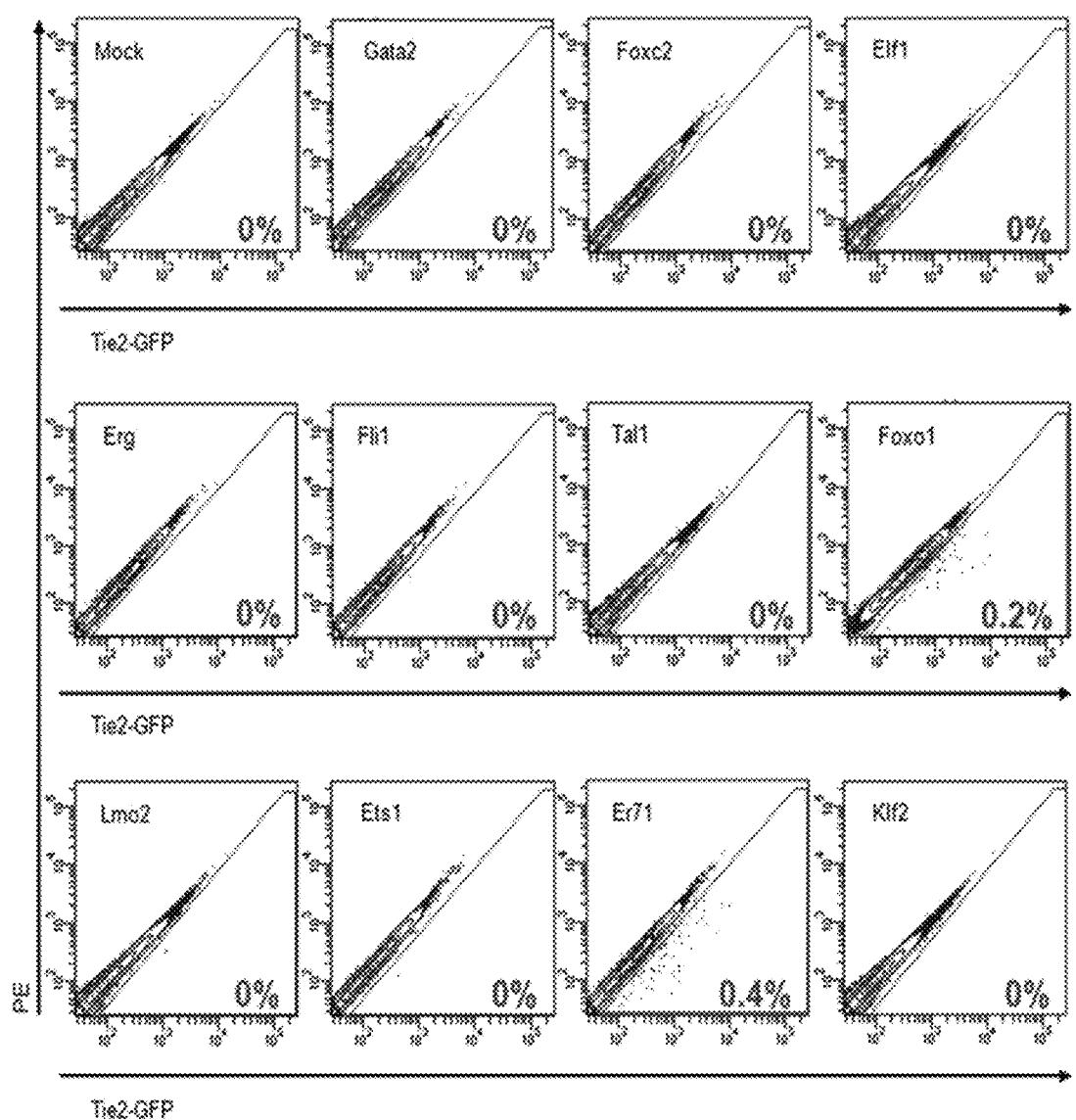

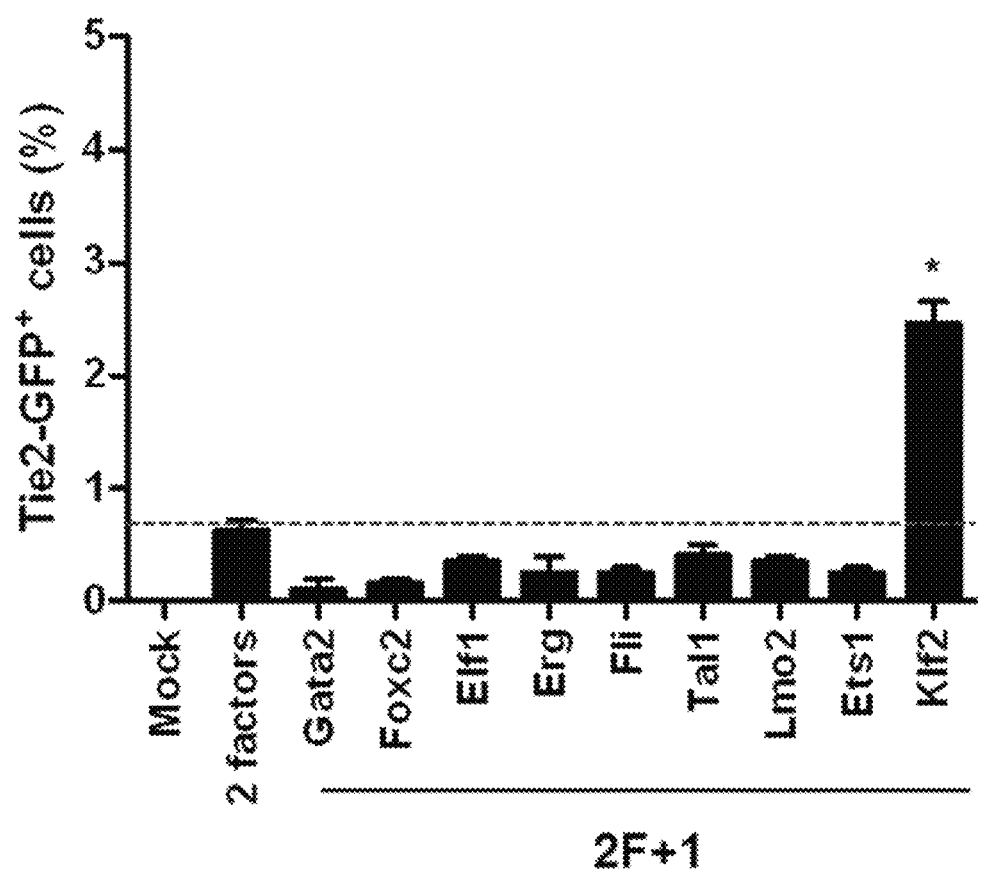
[Fig. 4]

[Fig. 5]
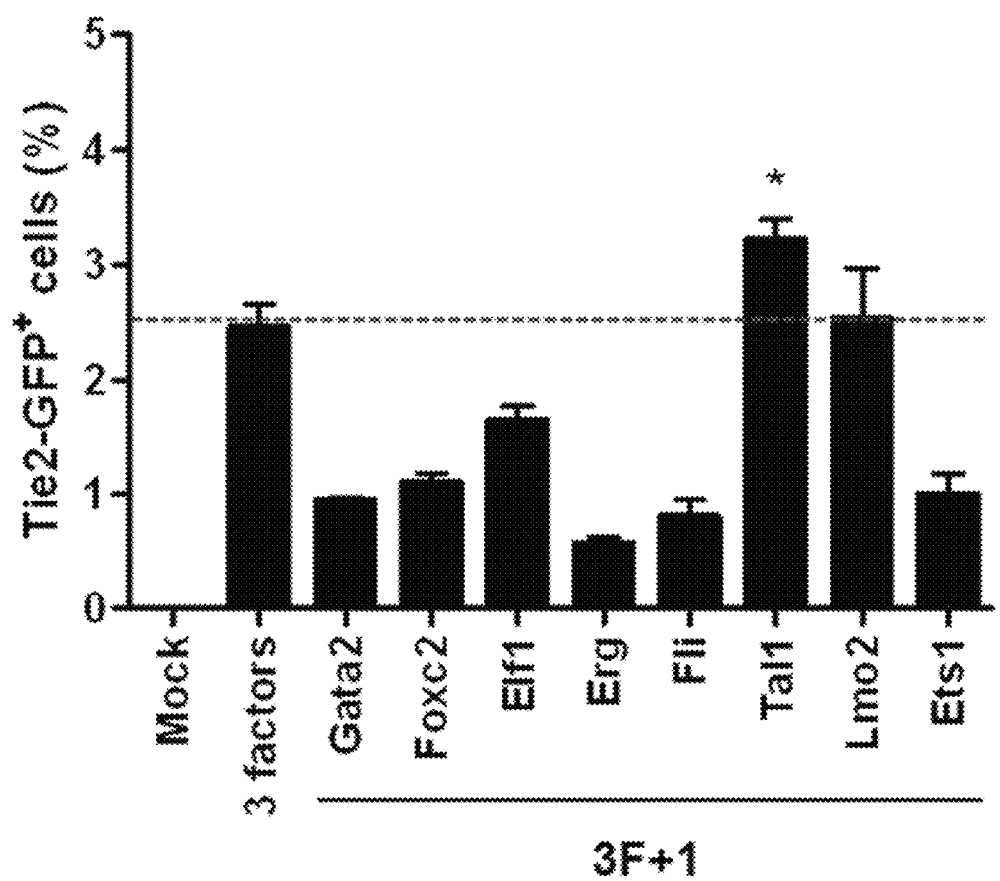

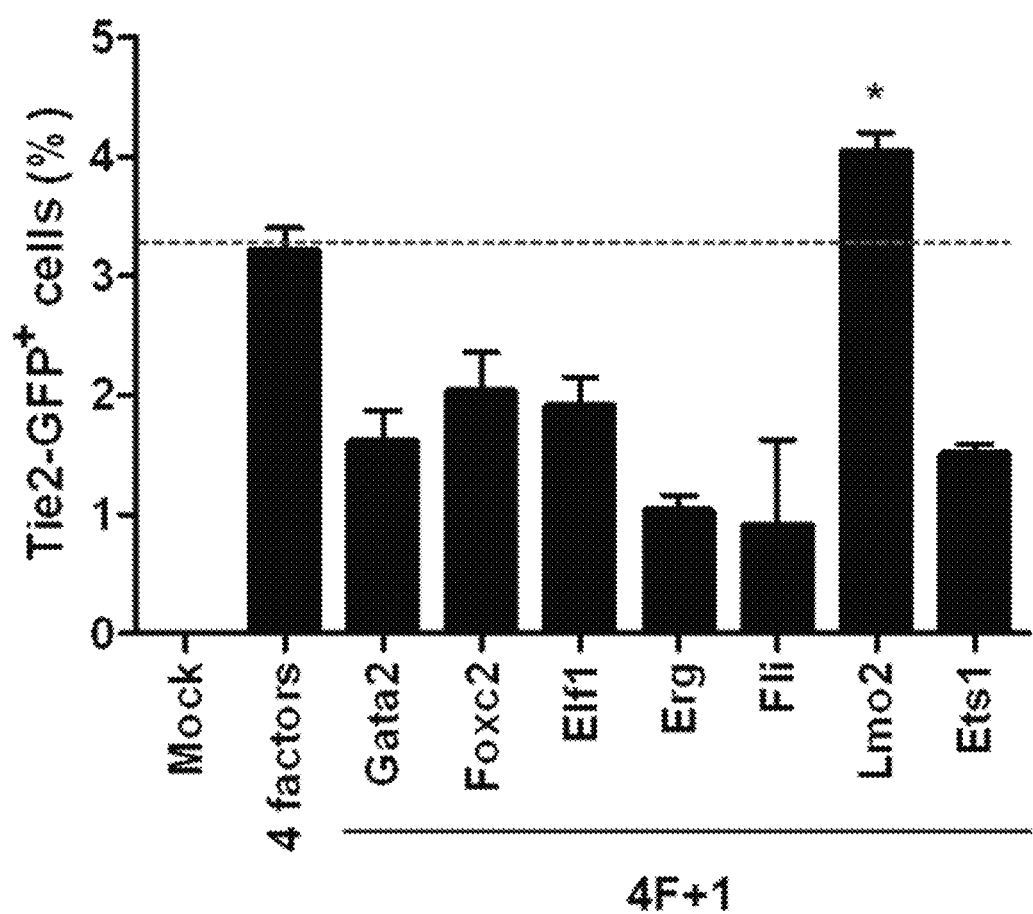
[Fig. 6]

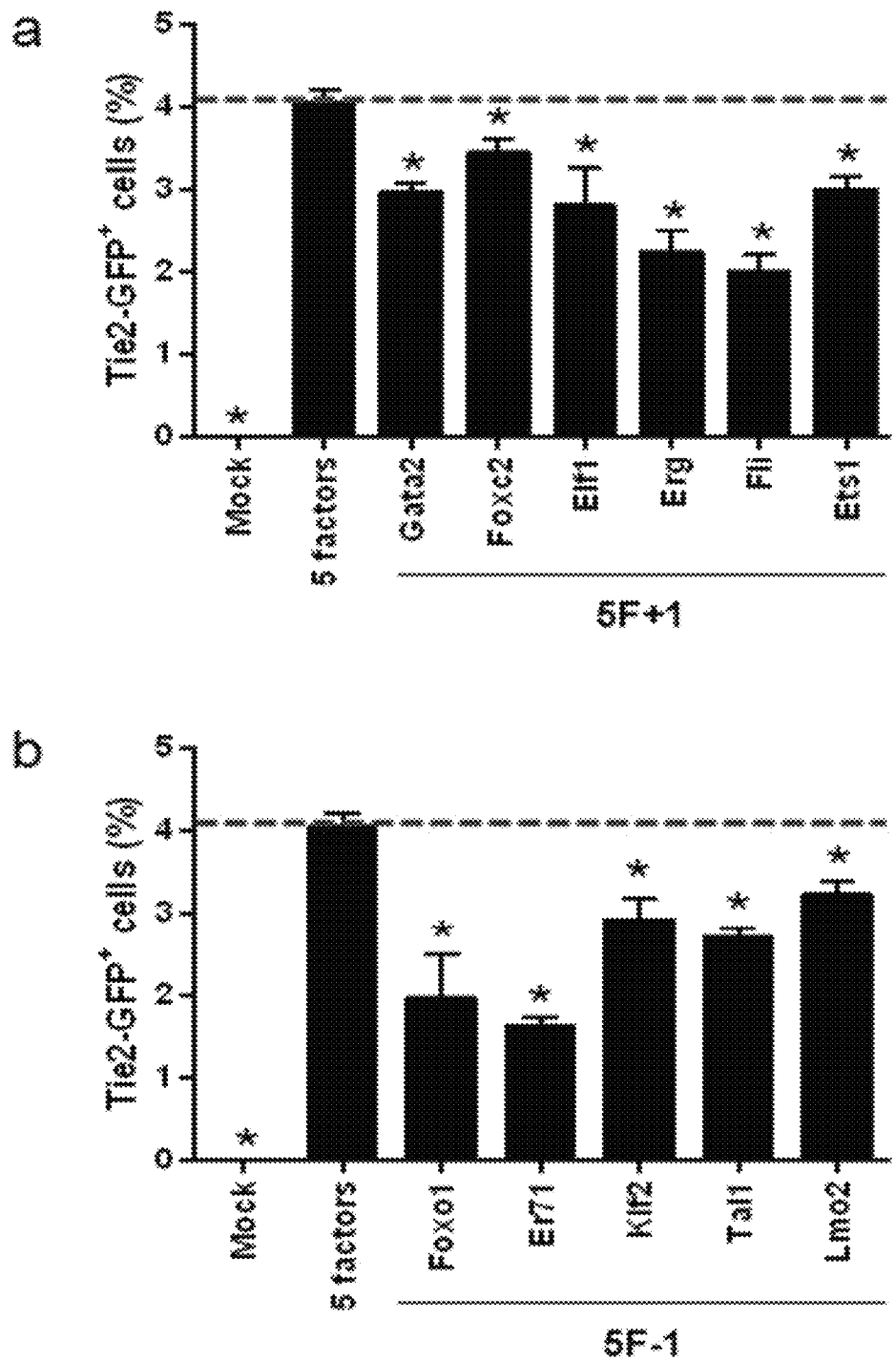
[Fig. 7]

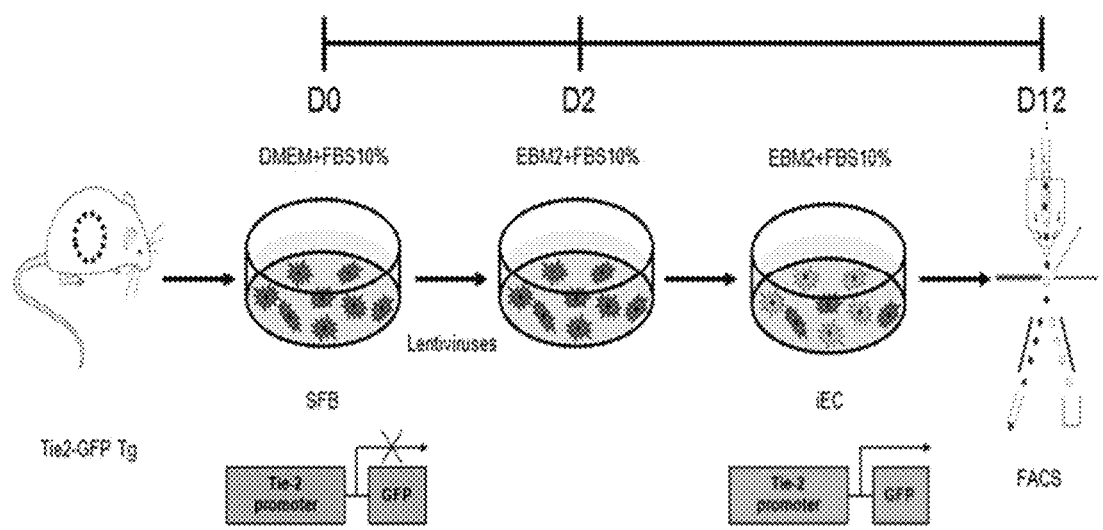
[Fig. 8]

[Fig. 9]
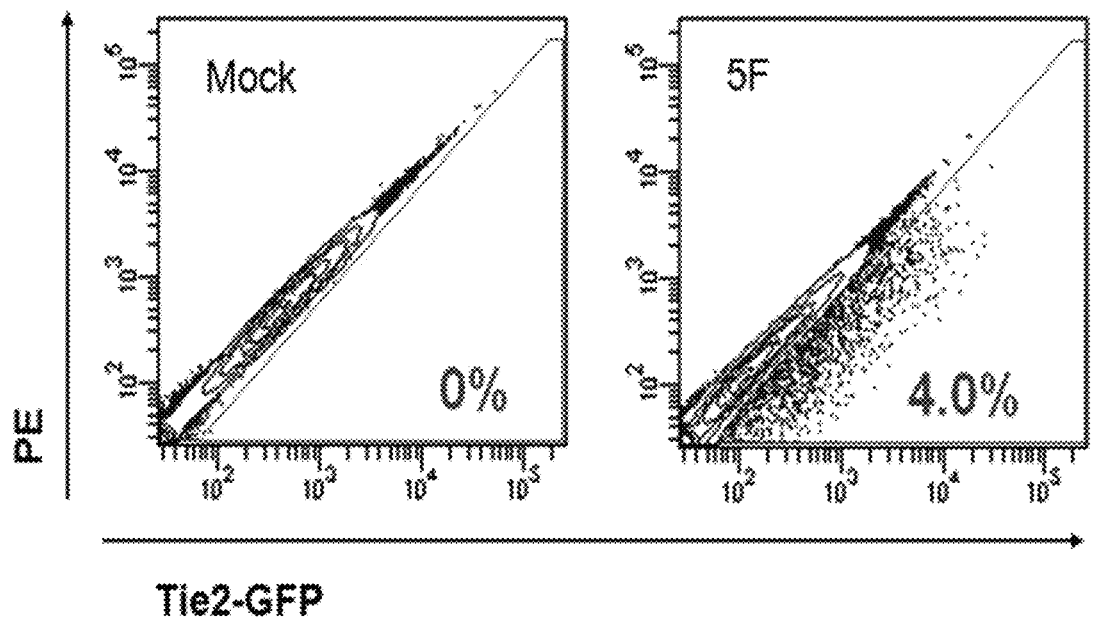
[Fig. 10]
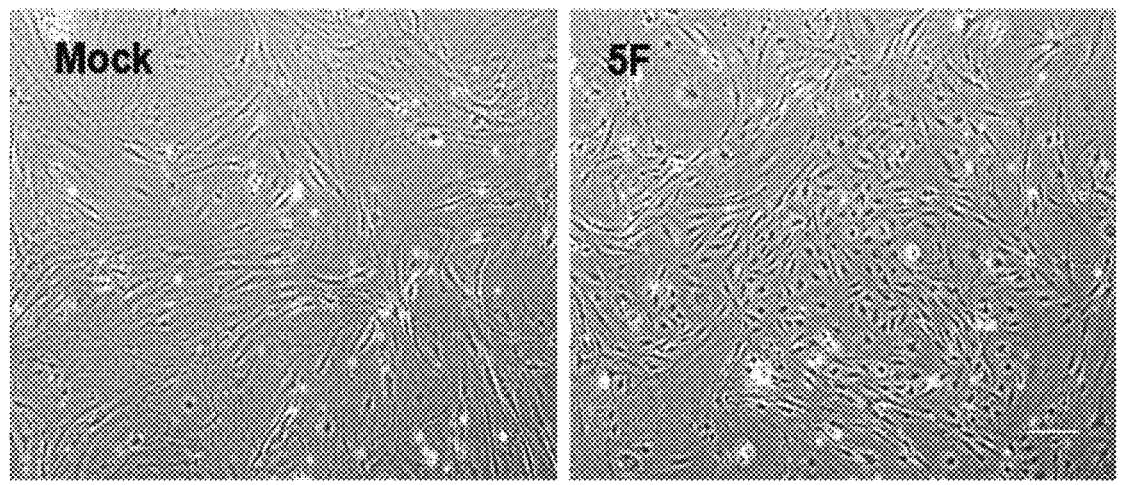

[Fig. 11]
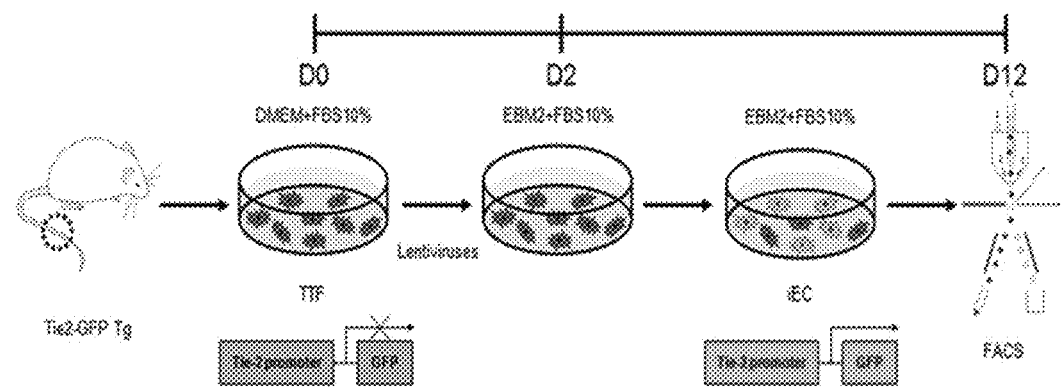
[Fig. 12]
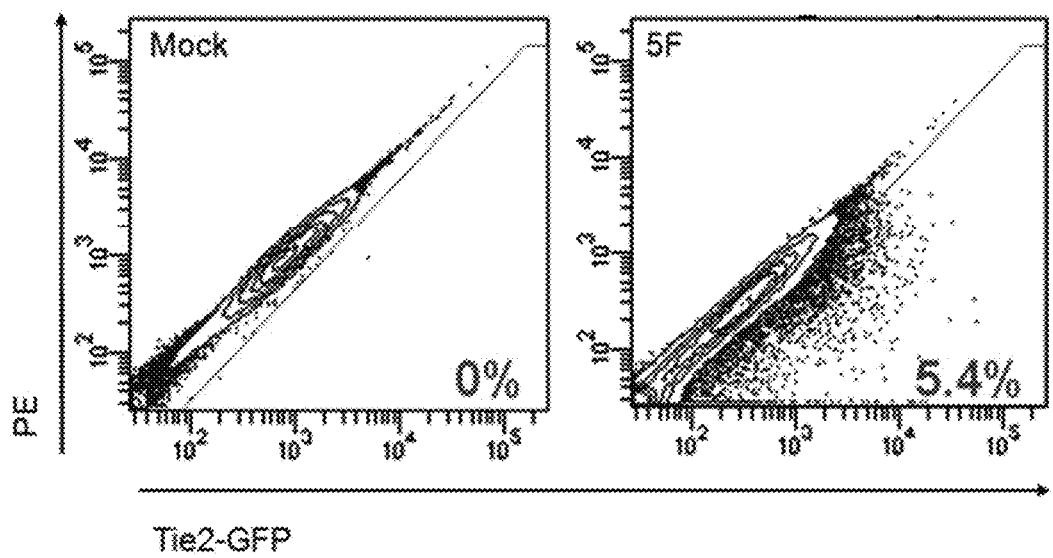

[Fig. 13]
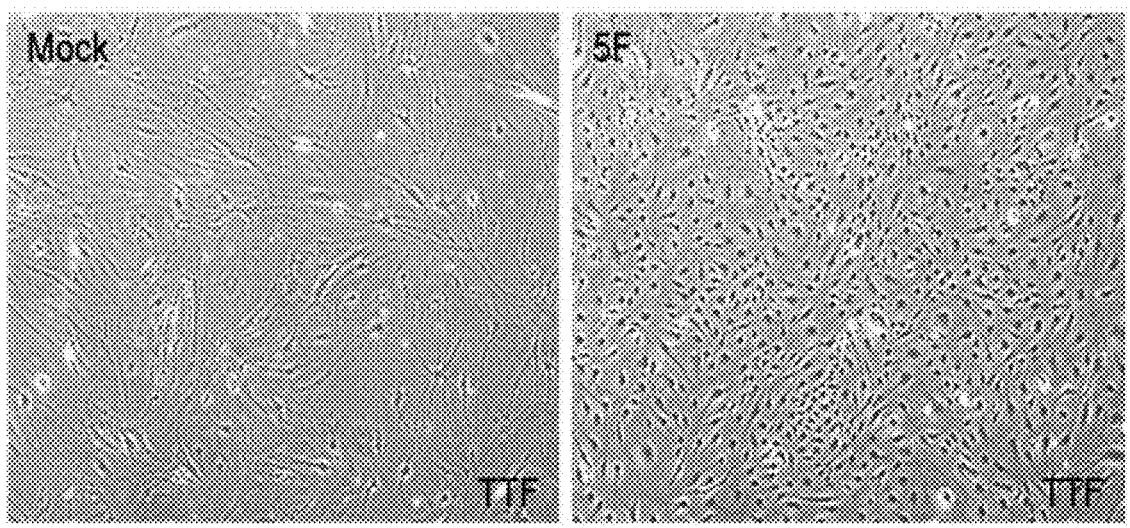

[Fig. 14]
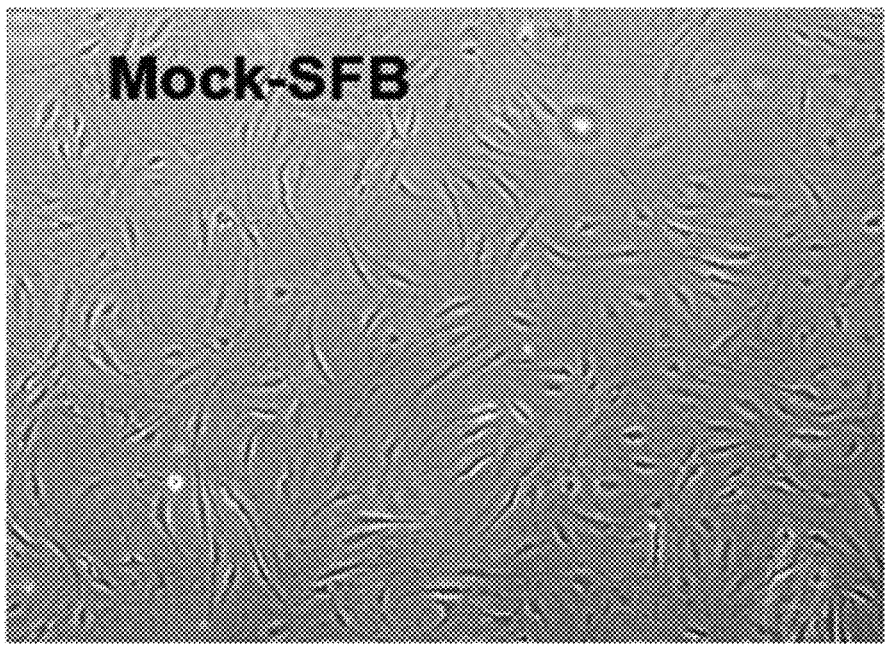
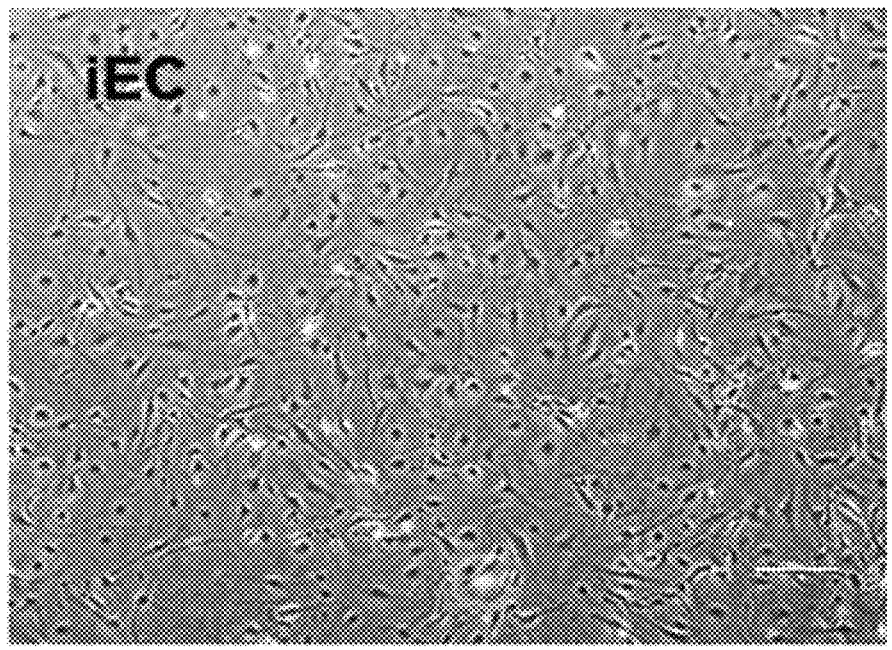

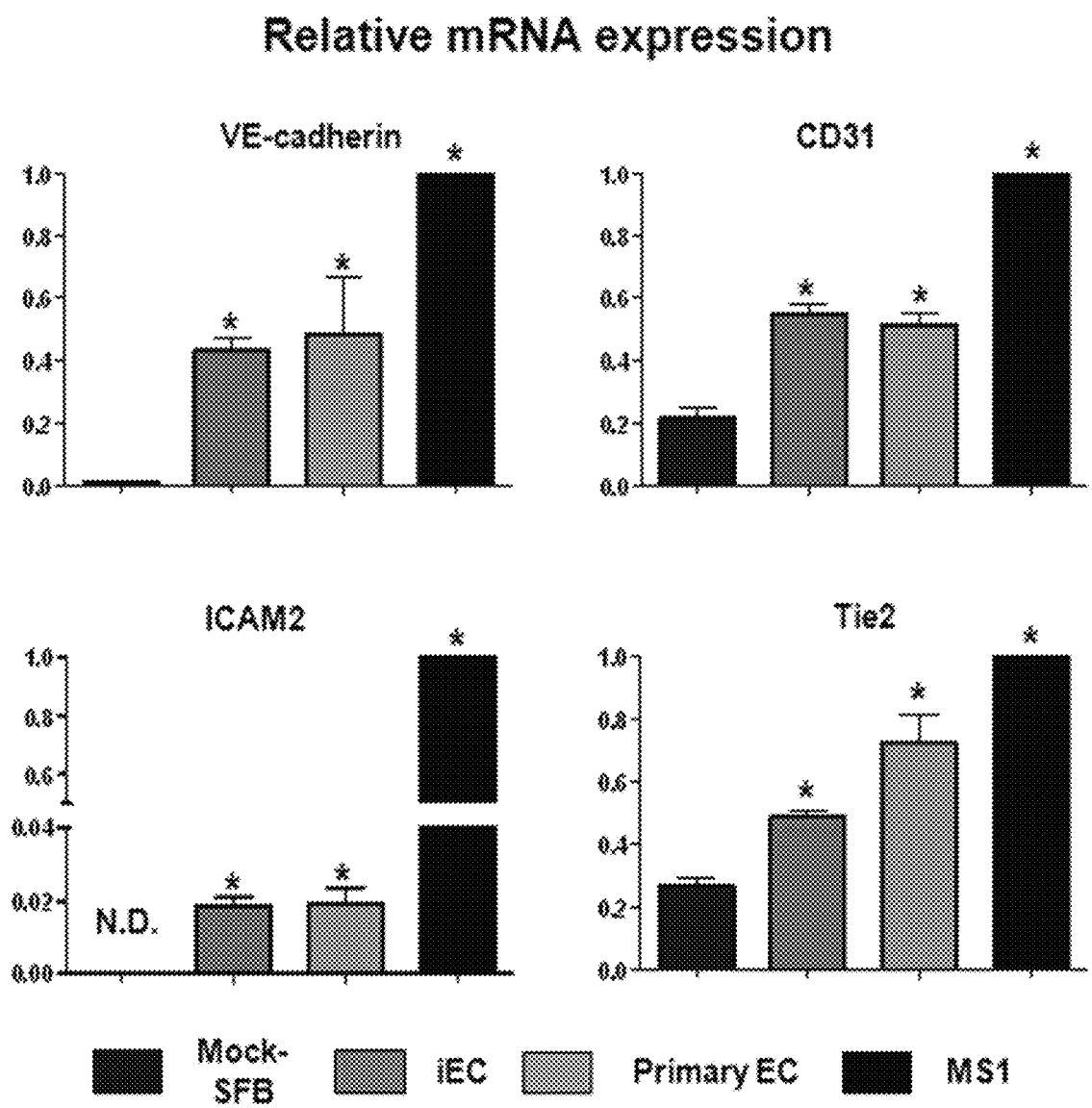
[Fig. 15]

[Fig. 16]
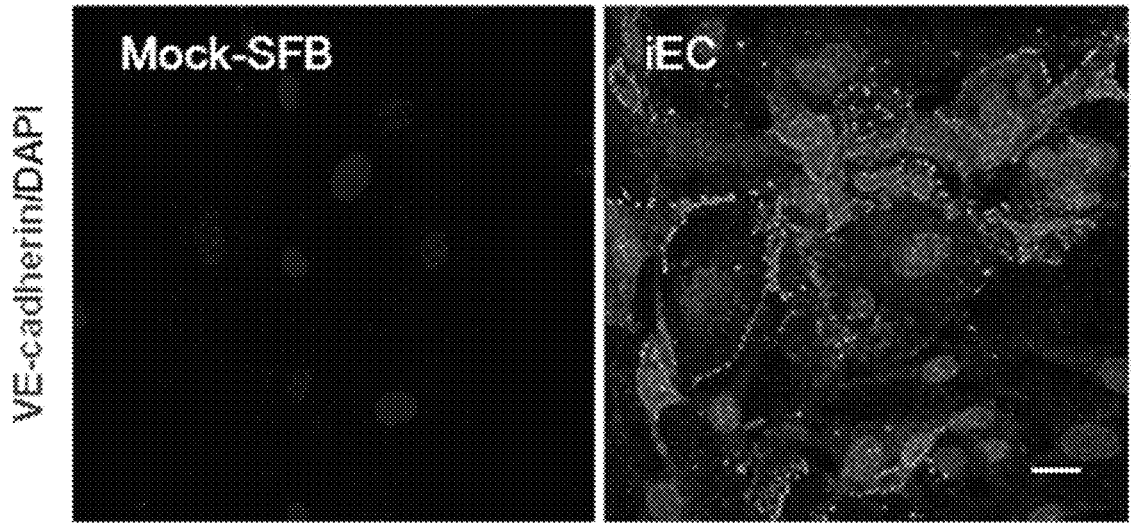
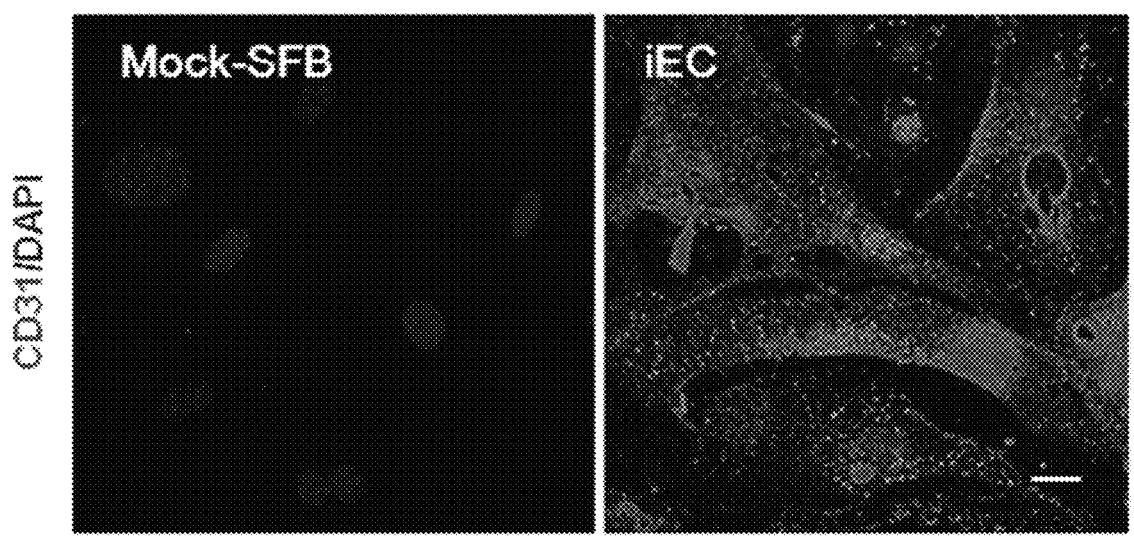

[Fig. 17]
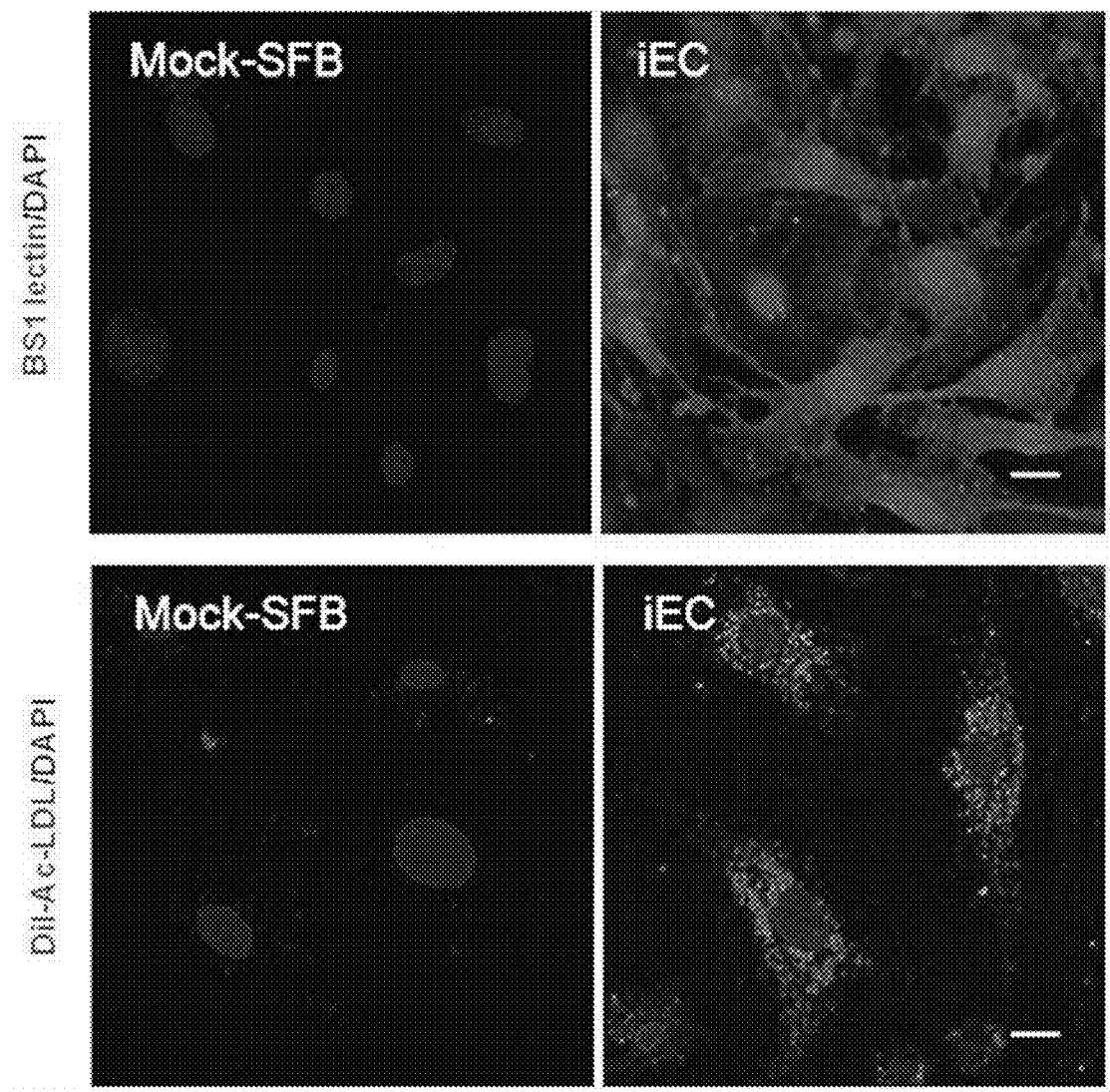

[Fig. 18]
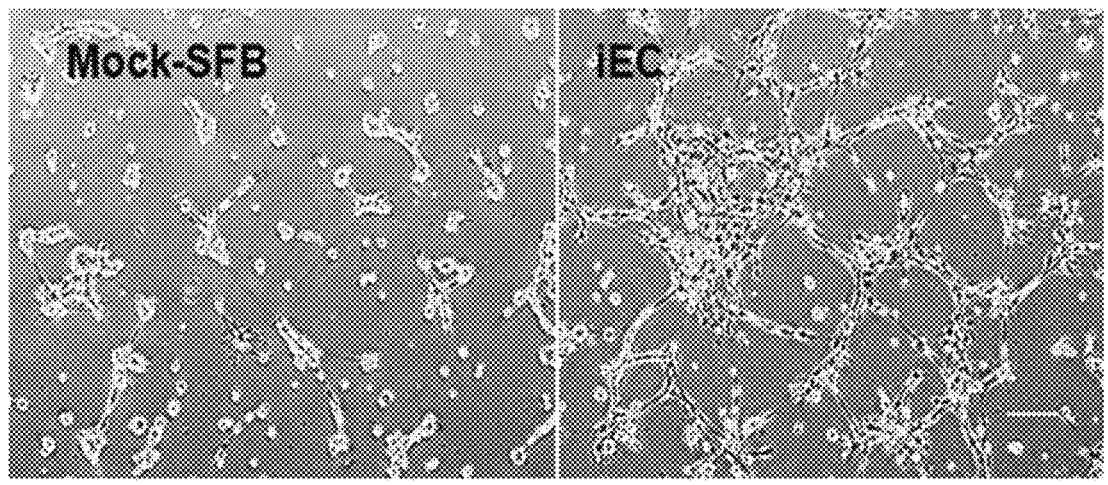
[Fig. 19]
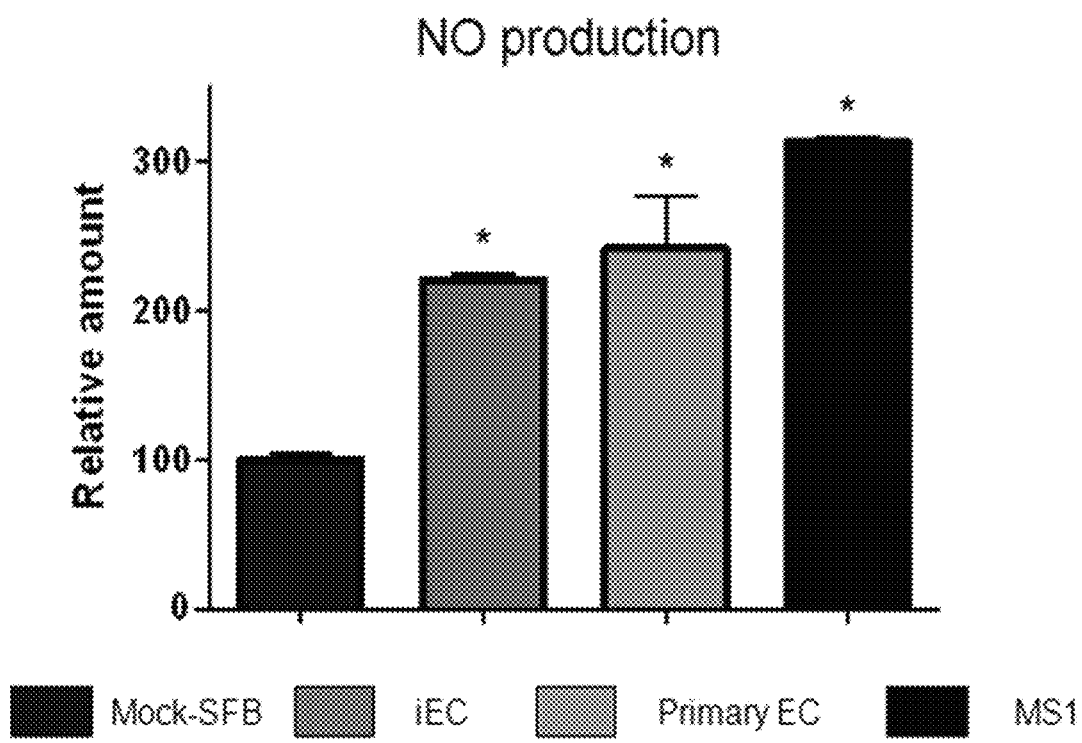

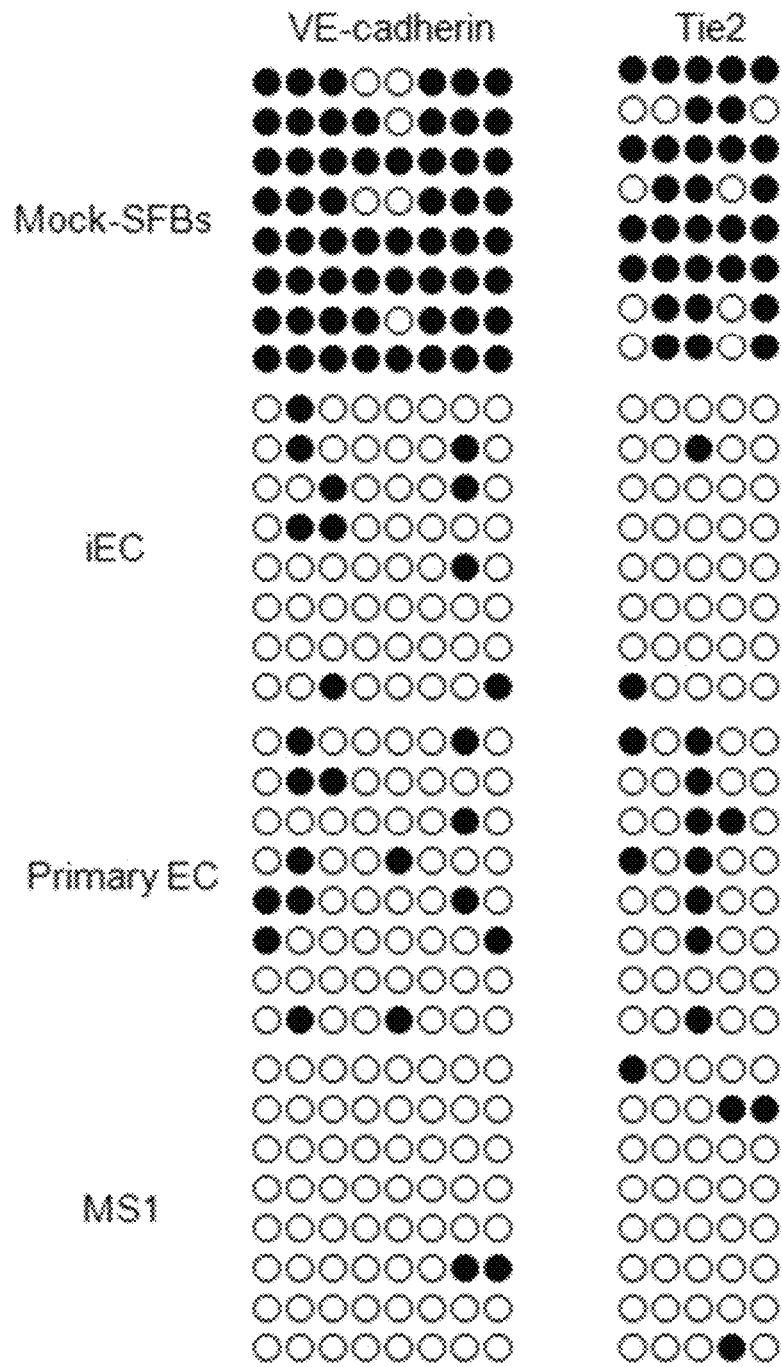

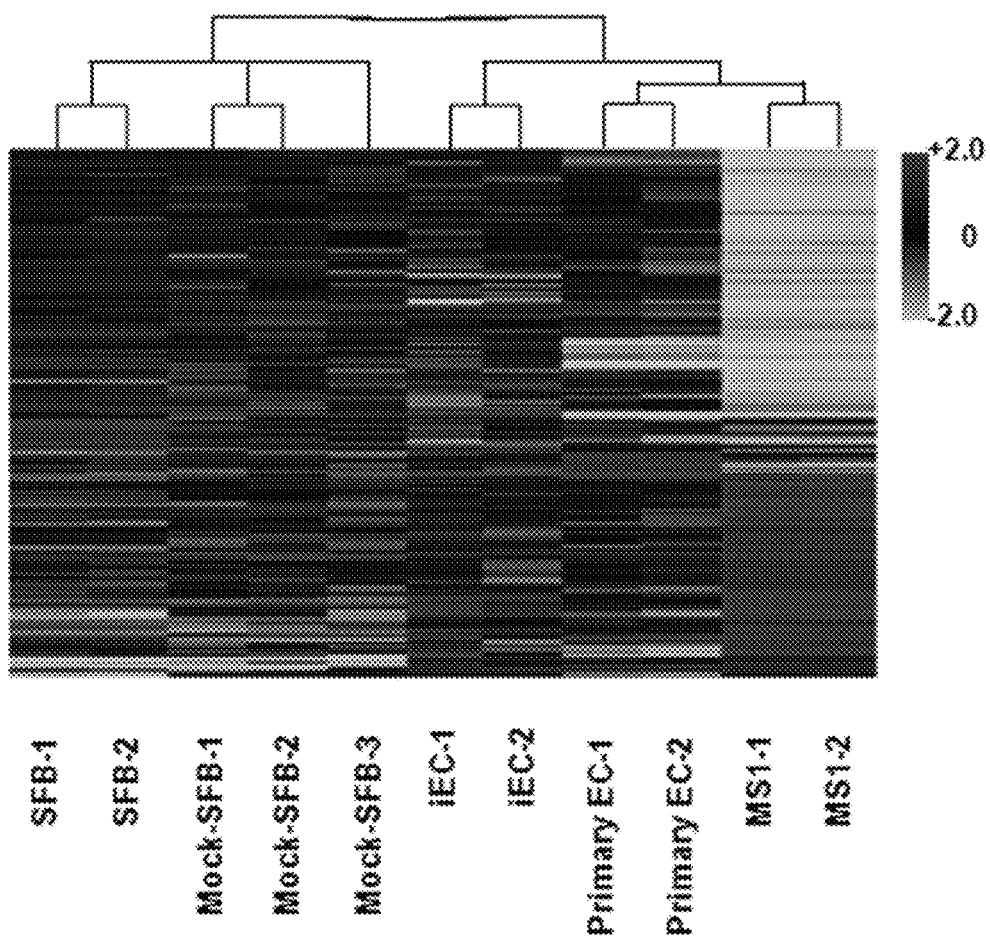

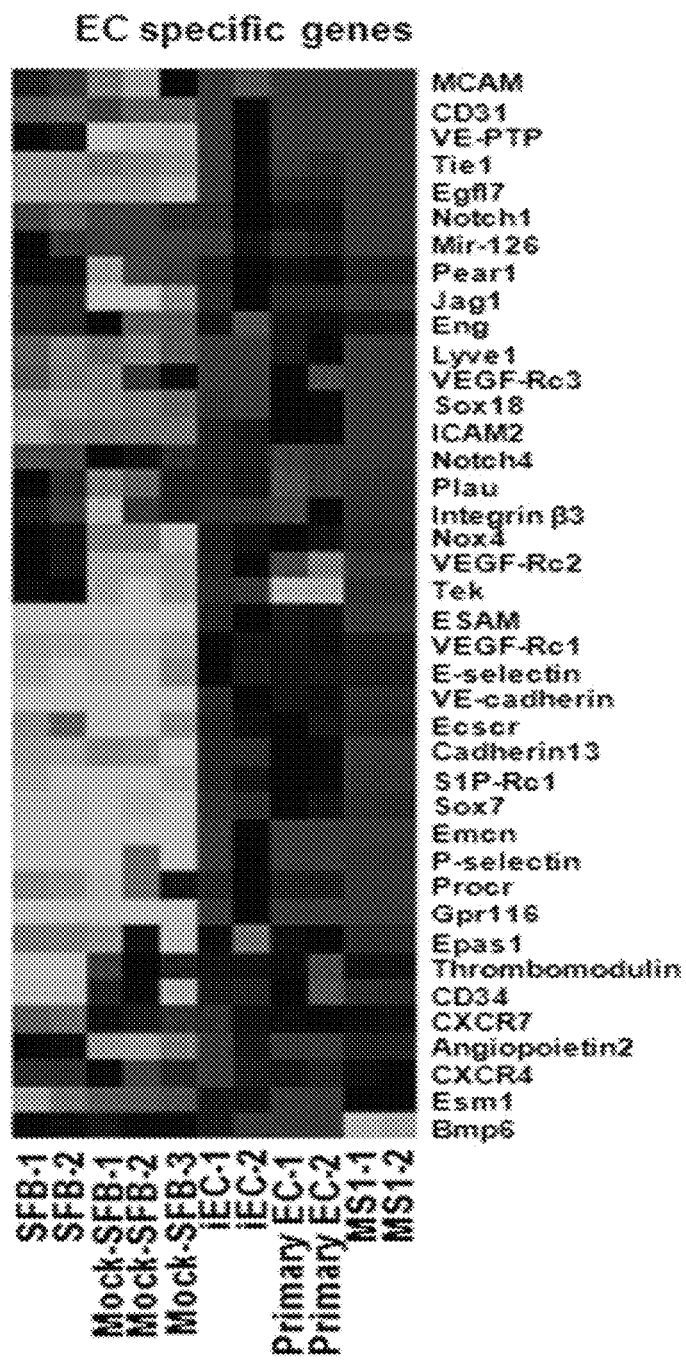
[Fig. 22]

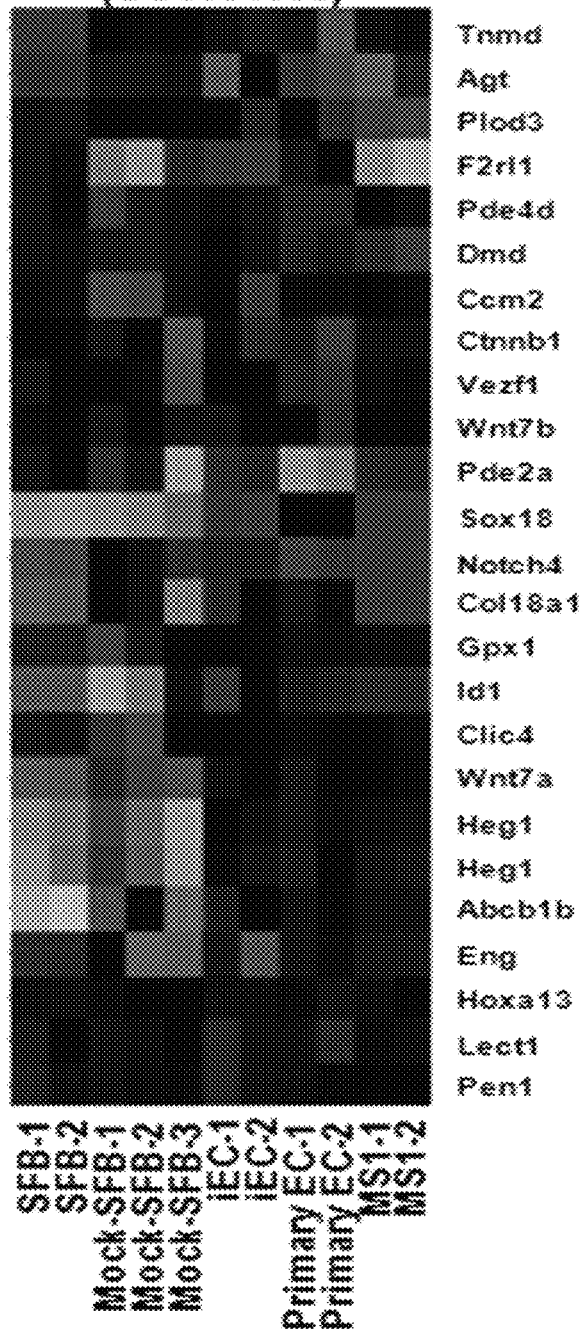
[Fig. 23]

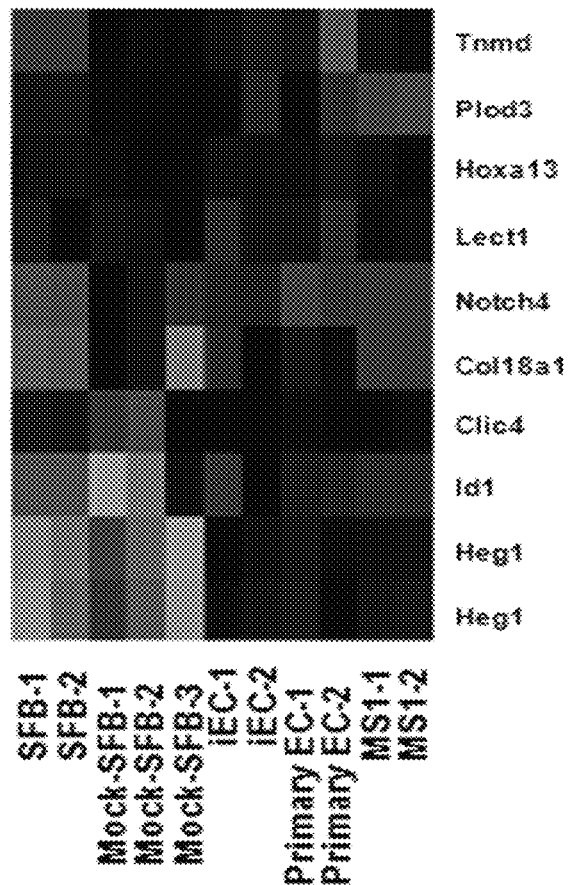
[Fig. 24]

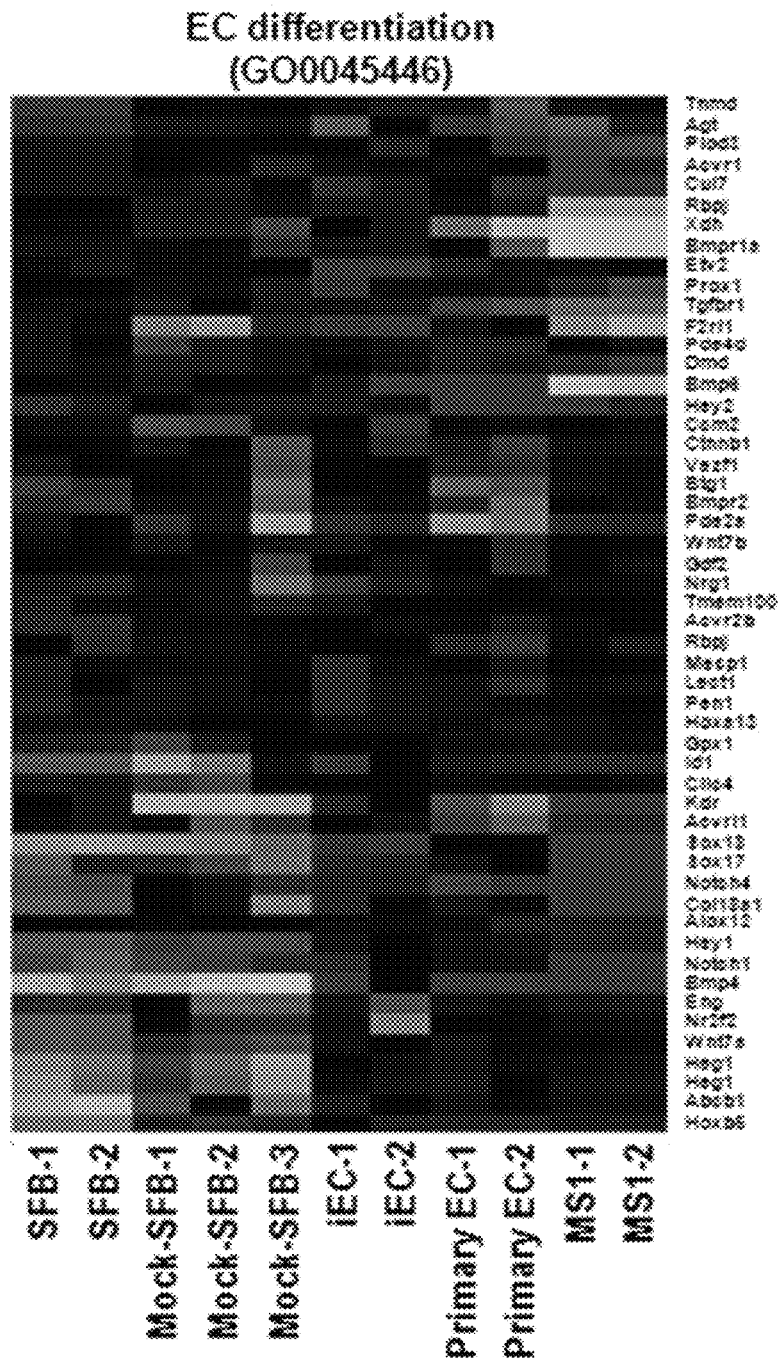
[Fig. 25]

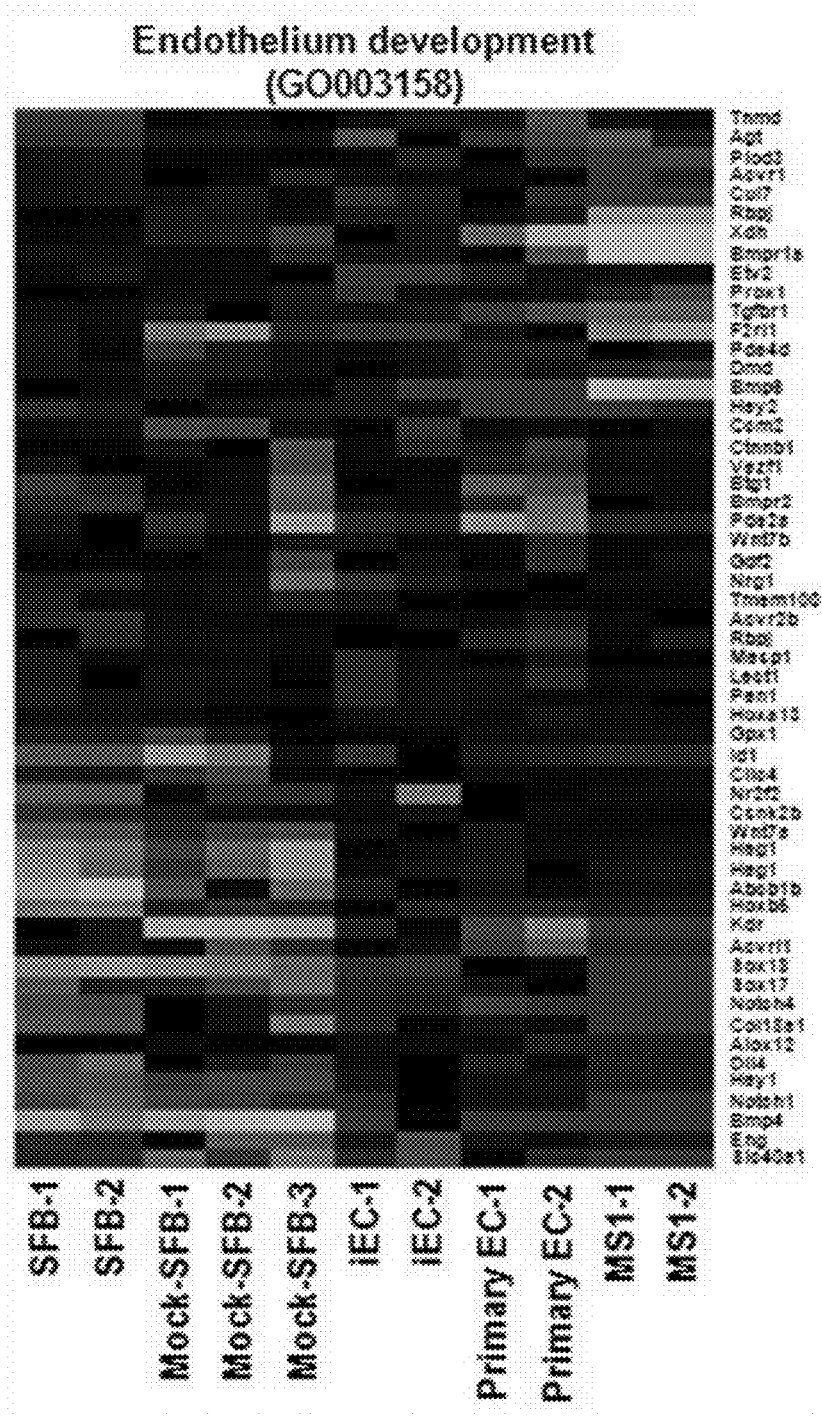
[Fig. 26]

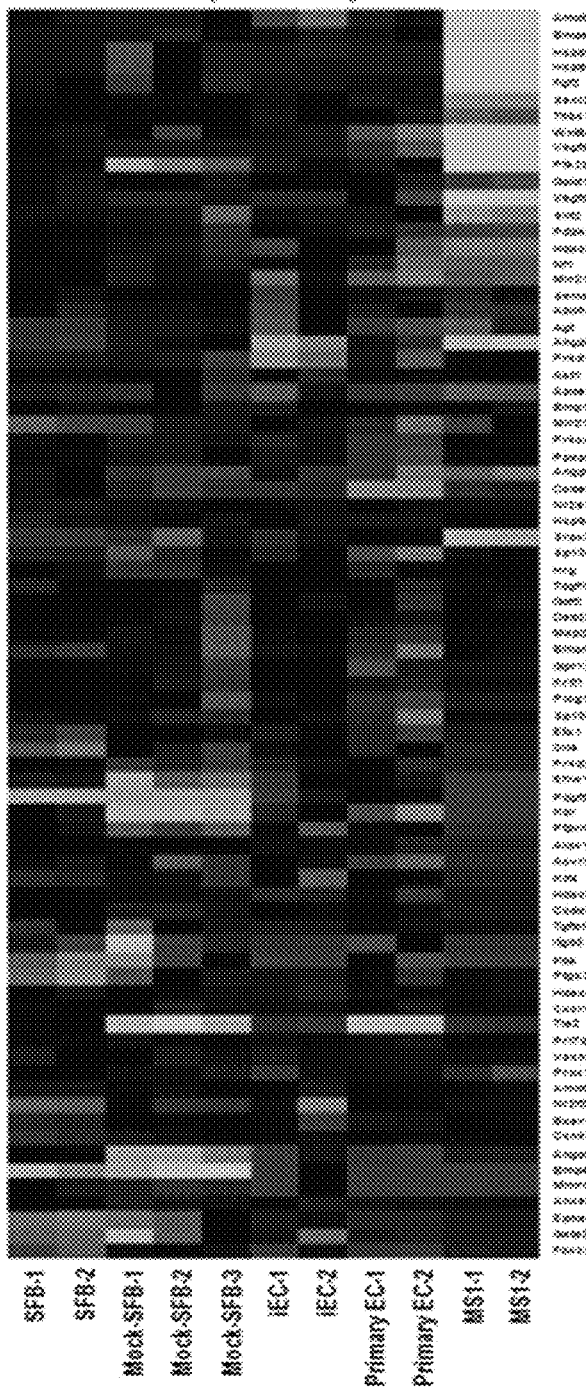
[Fig. 27]

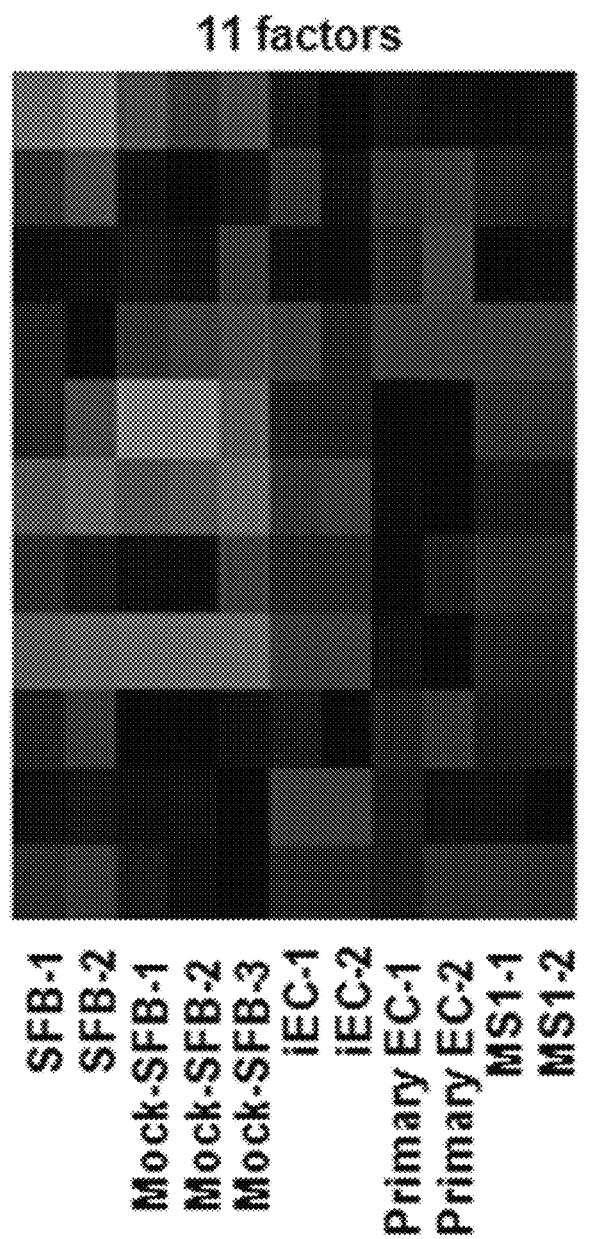
[Fig. 28]

[Fig. 29]
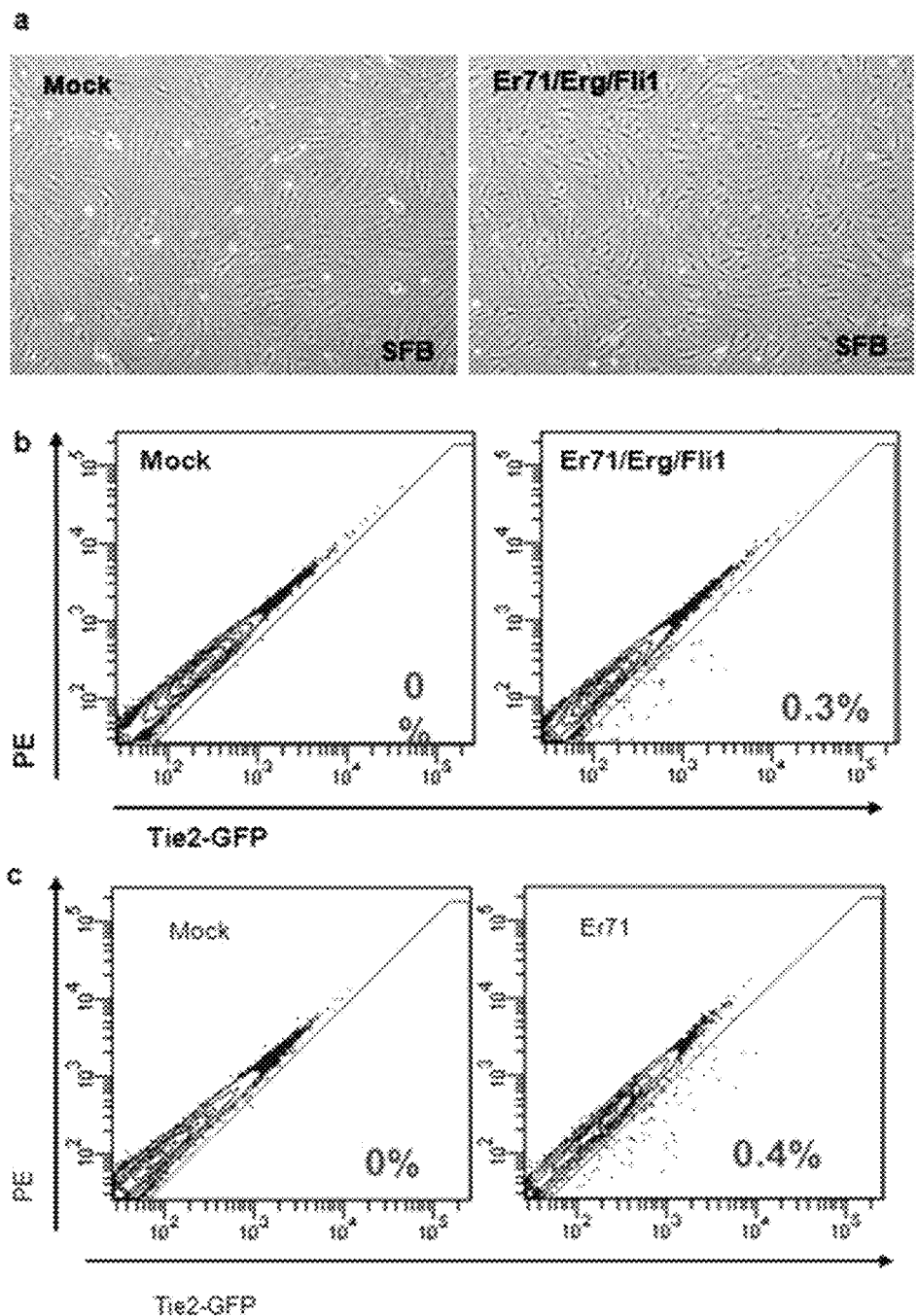

[Fig. 30]
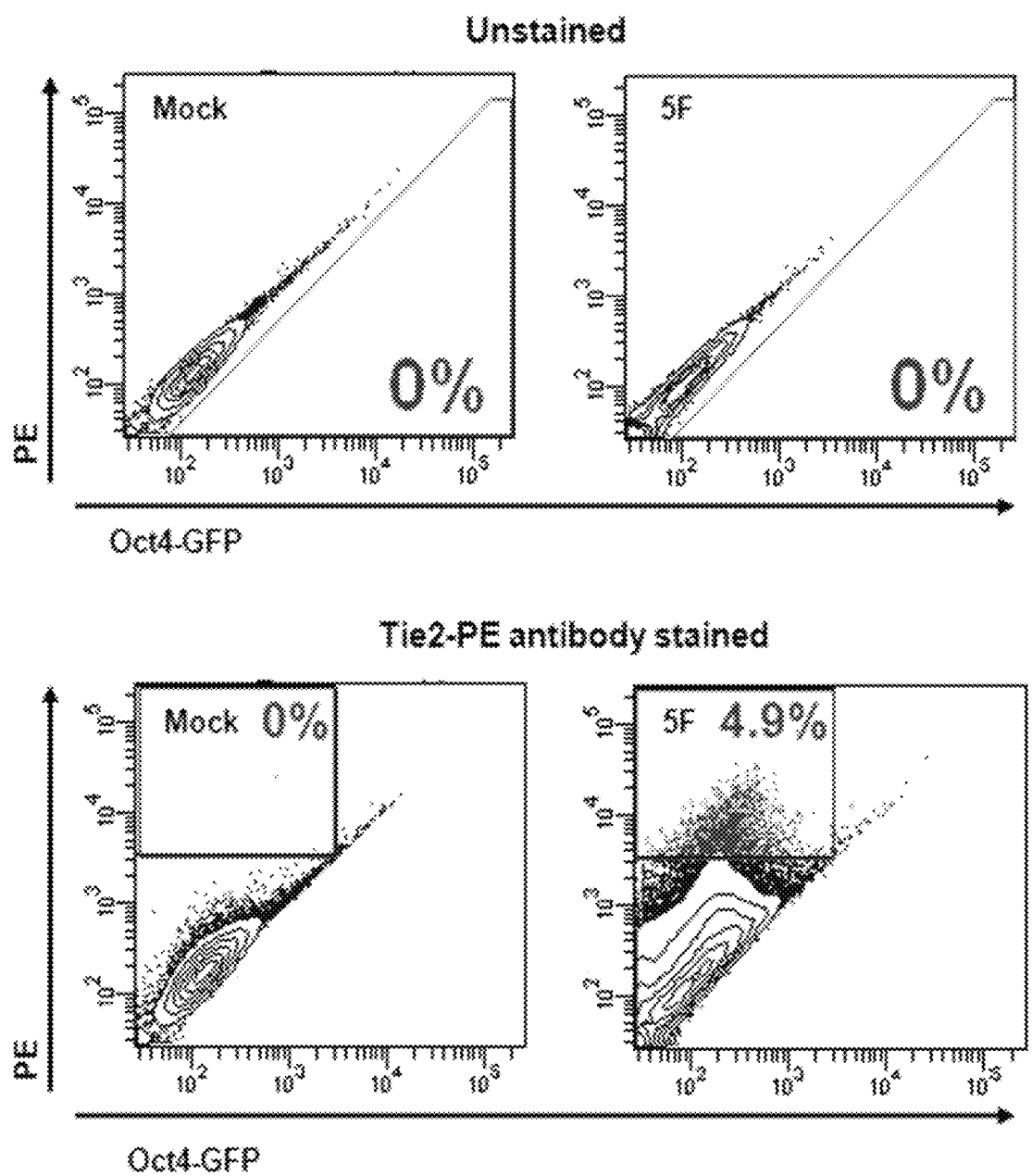

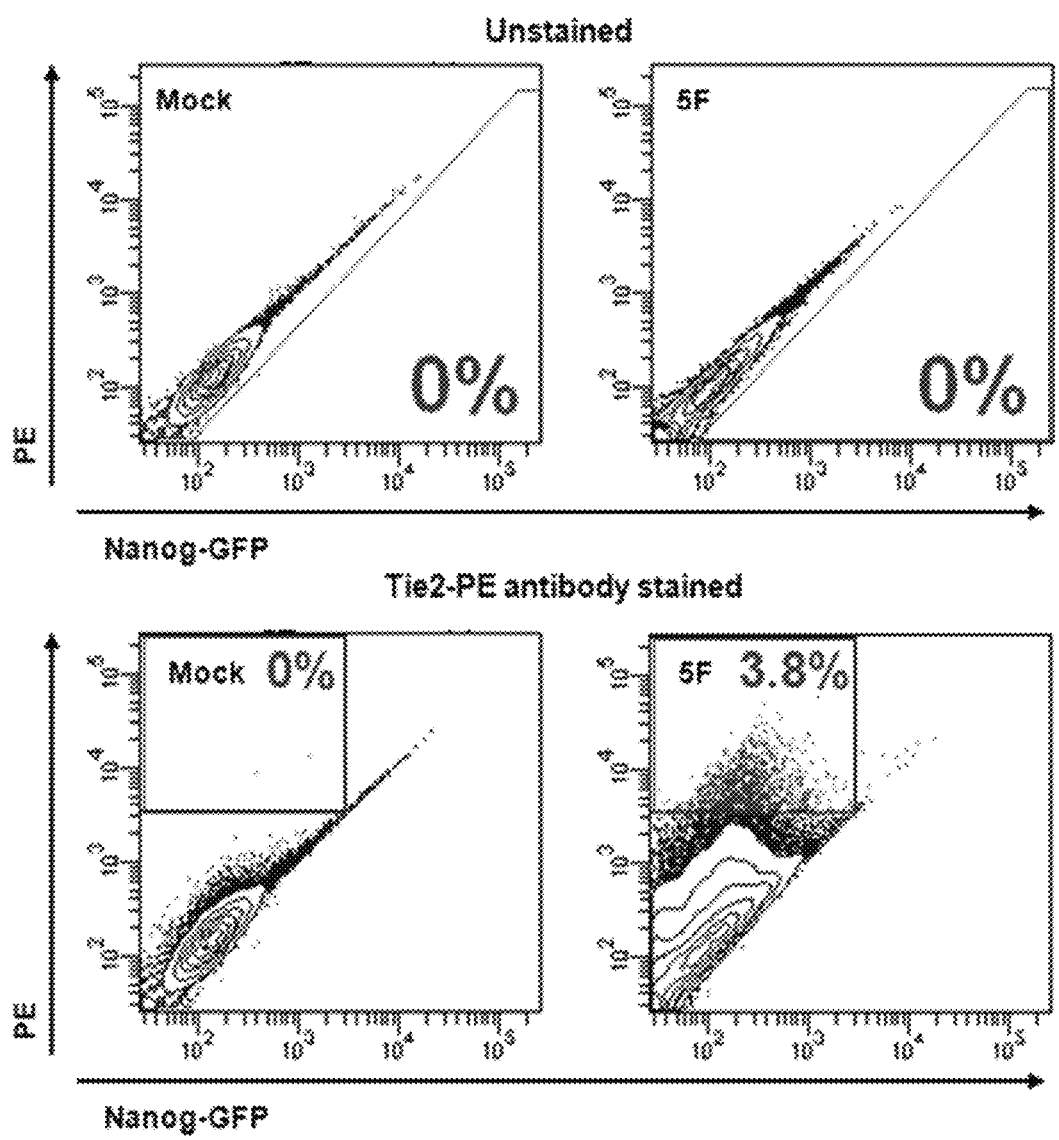
[Fig. 31]

[Fig. 32]
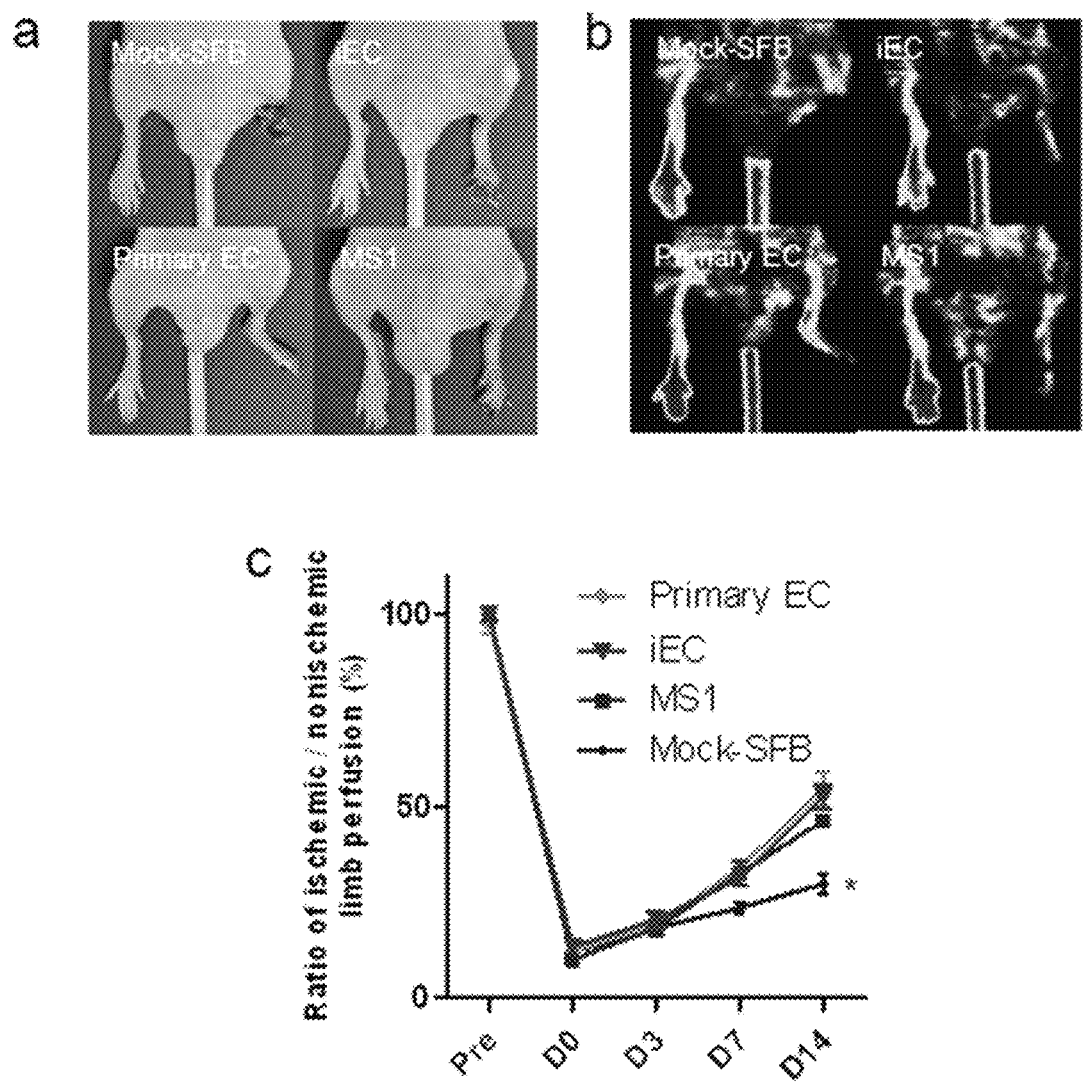

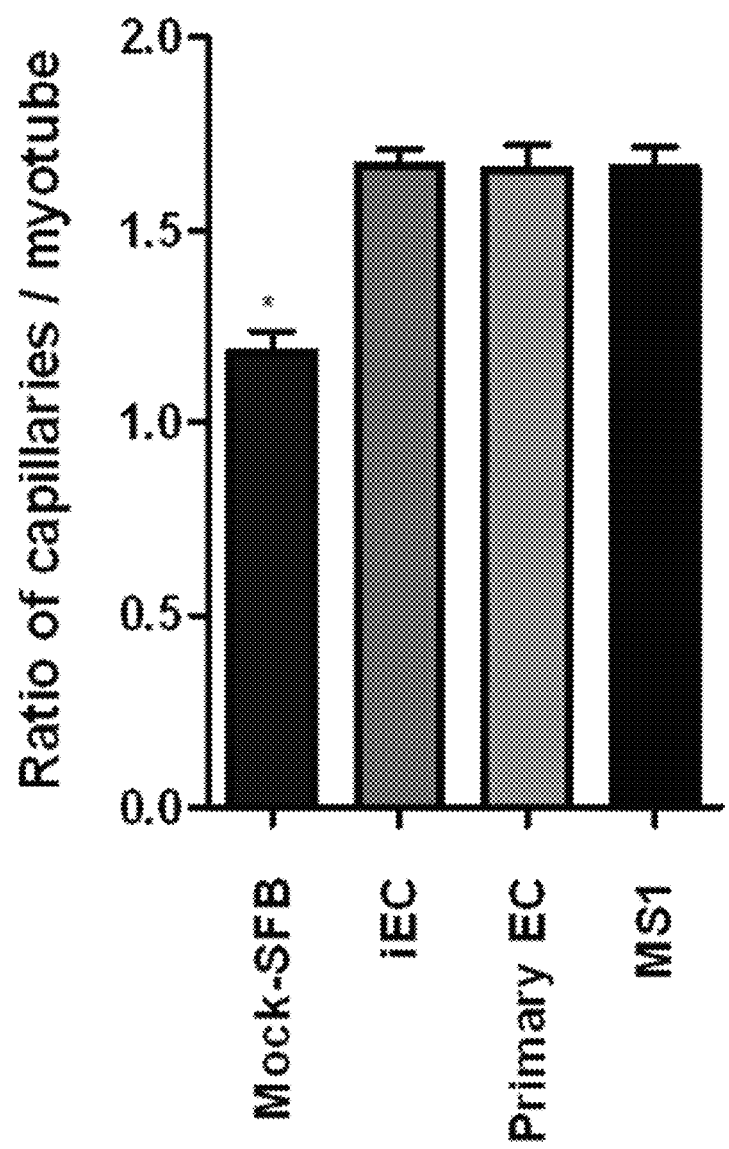
[Fig. 33]

[Fig. 34]
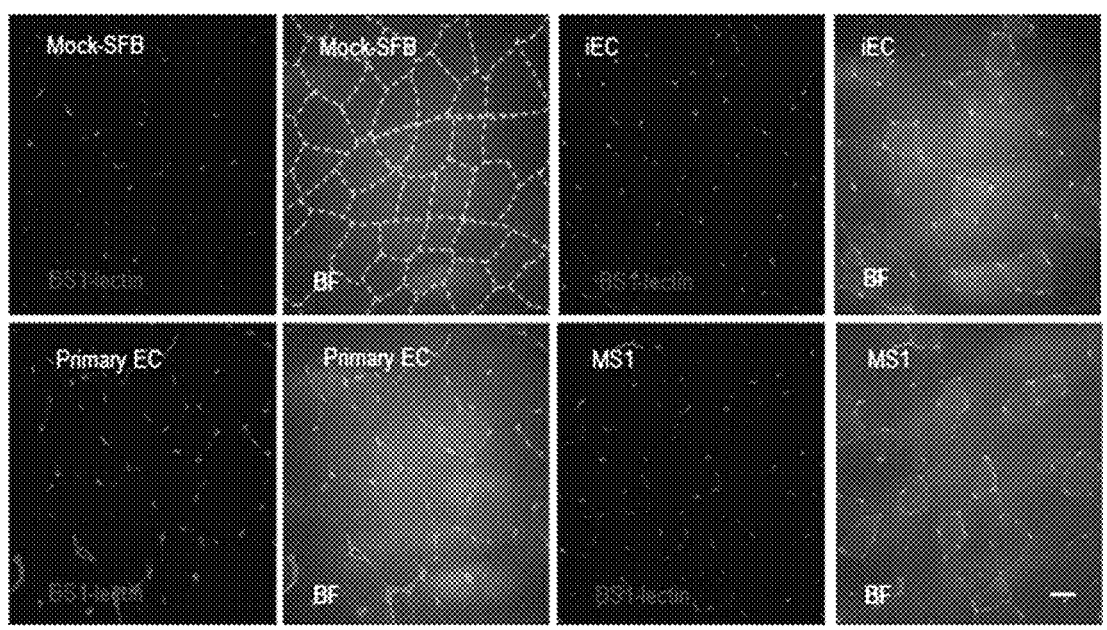

[Fig. 35]
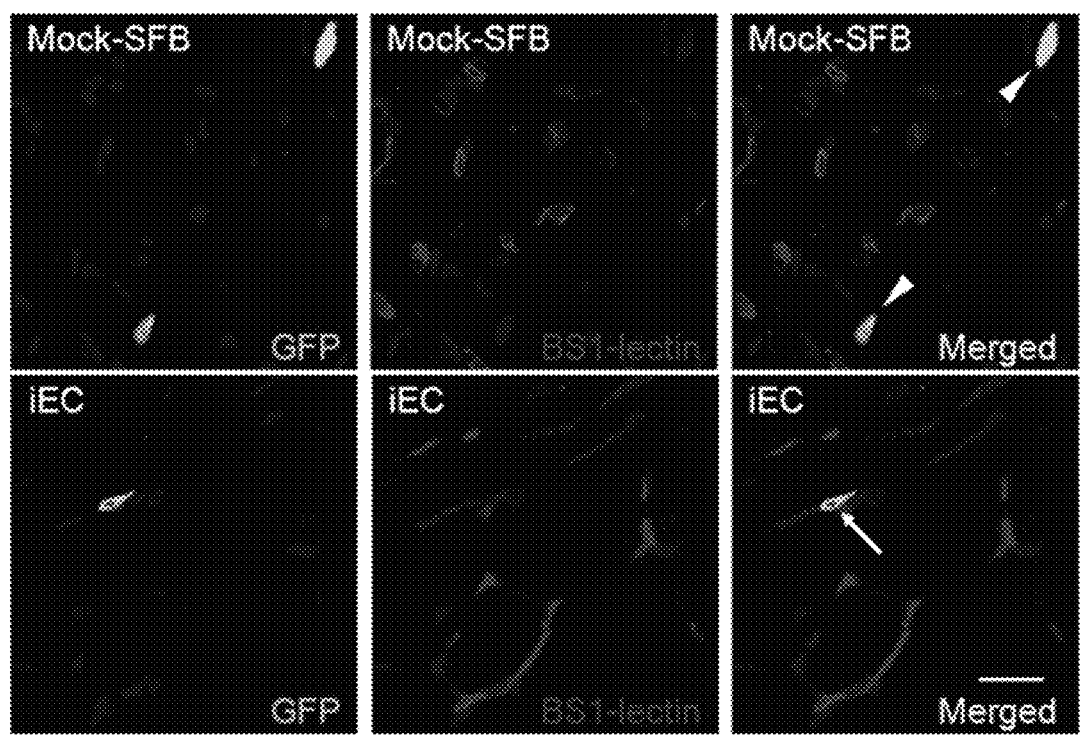

[Fig. 36]
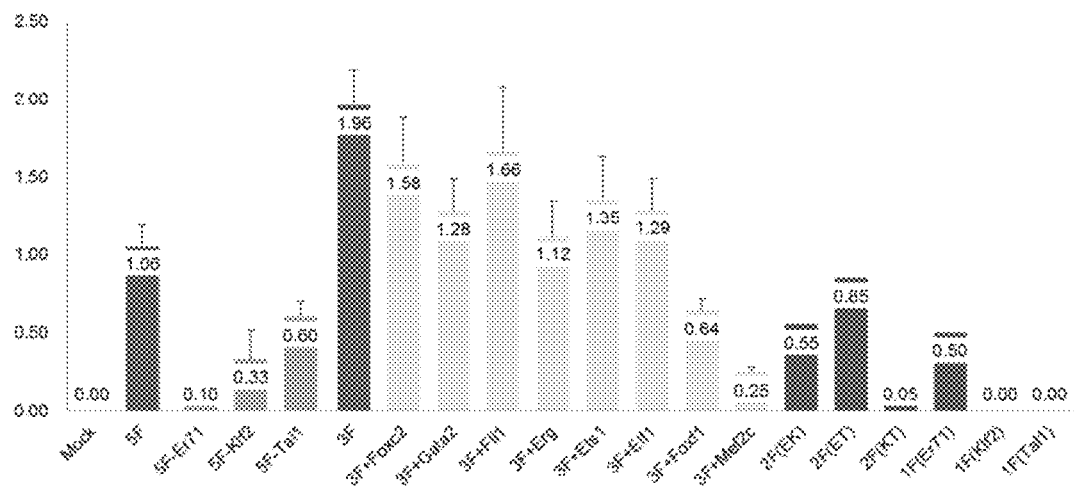
[Fig. 37]
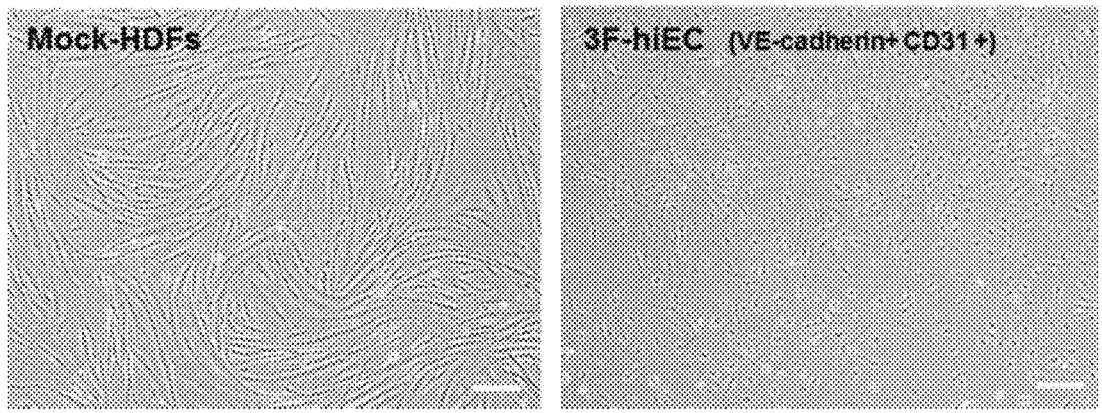

[Fig. 38]
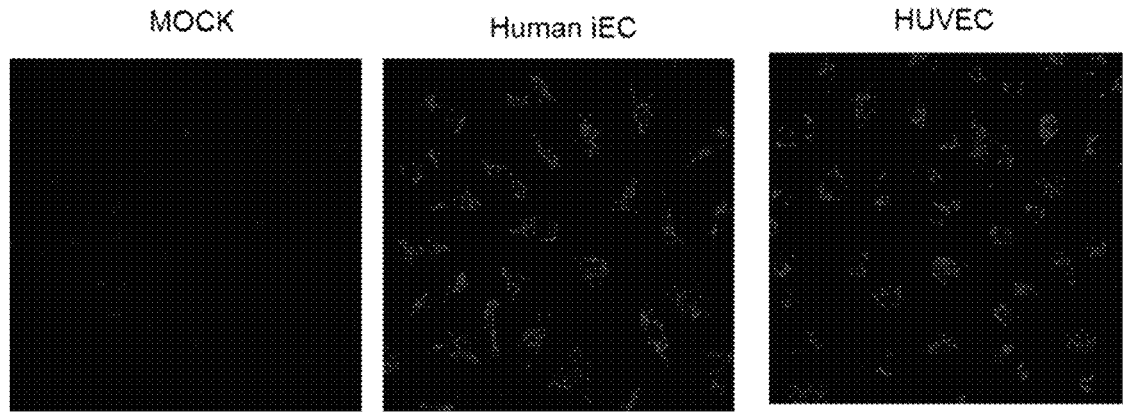
[Fig. 39]
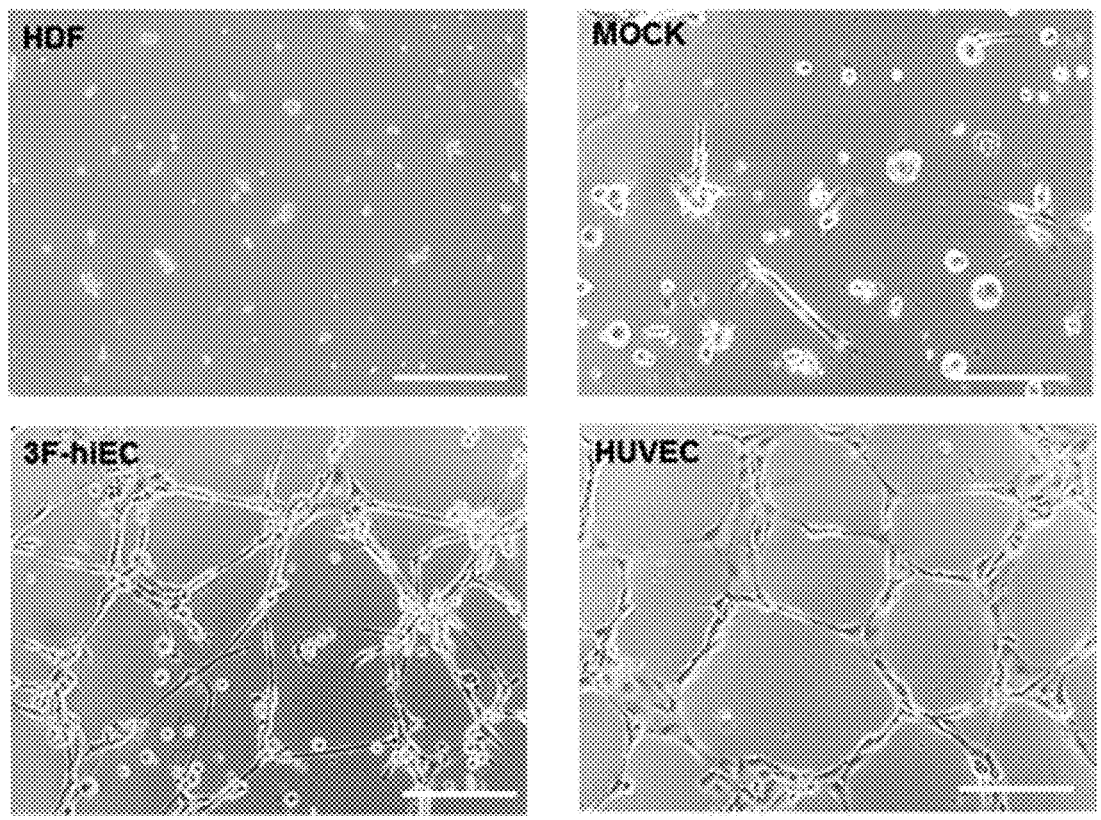

[Fig. 40]
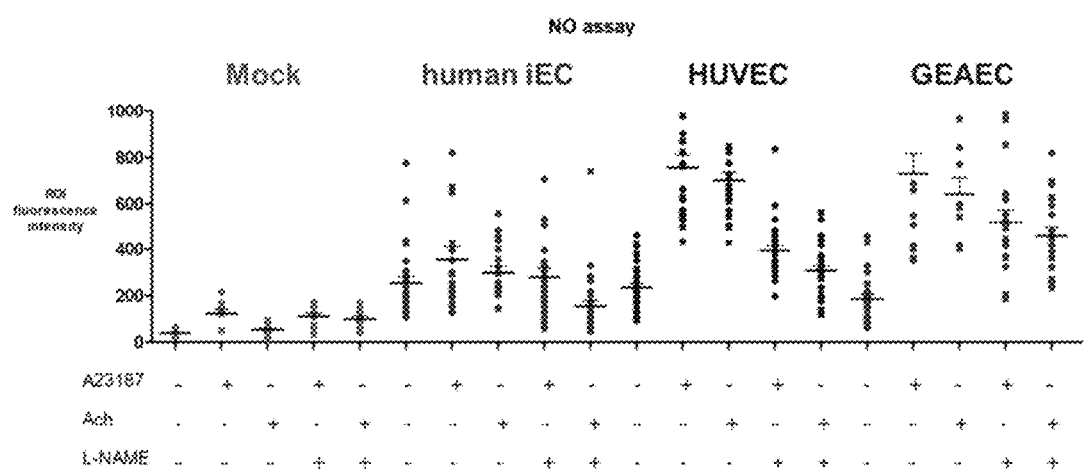
[Fig. 41]
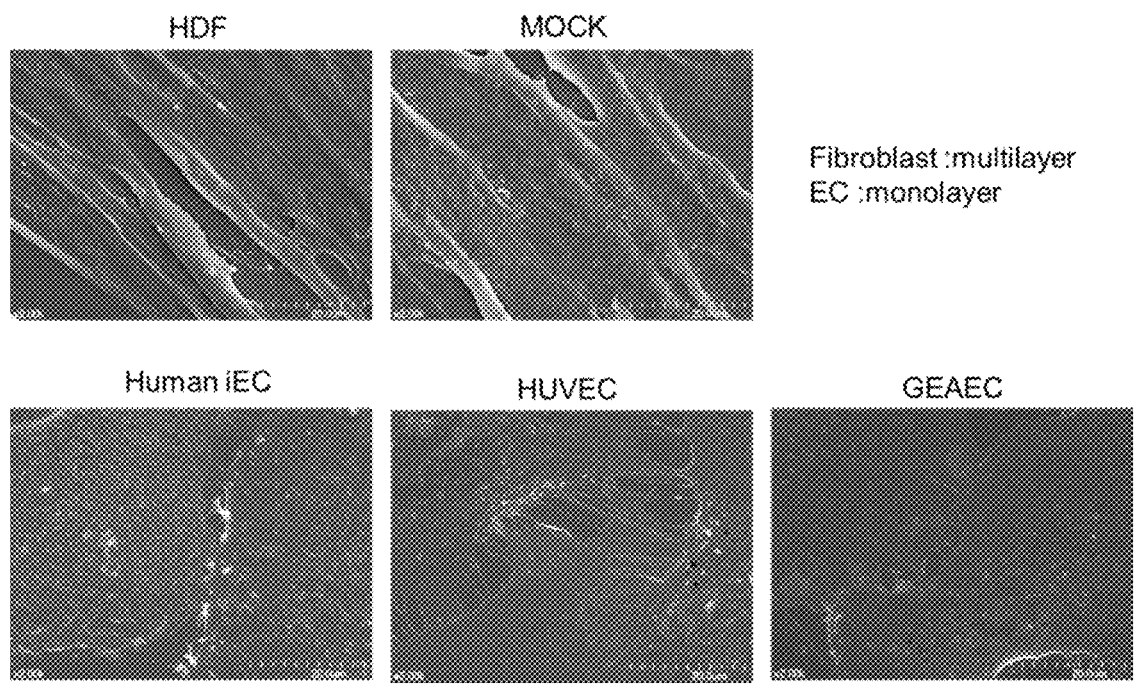

METHOD FOR PREPARING OF ENDOTHELIAL CELLS BY TRANSFORMATION (TRANSDIFFERENTIATION) OF ADULT FIBROBLAST, AND USE THEREOF

CROSS-REFERENCE TO RELATED APPLICATION

This application claims priority to and the benefit of Korean Patent Application No. 10-2013-0138570, filed on Nov. 14, 2013 and International Patent Application No. PCT/KR2014/010740, filed on Nov. 10, 2014, the disclosure of which is incorporated herein by reference in its entirety.

The present invention was undertaken with the support of Innovative Research Institute for Cell Therapy No. A062260 grant funded by the Ministry of Health and Welfare, Republic of Korea and Bio & Medical Technology Development Program NRF-2015M3A9B4051041 grant of the National Research Foundation (NRF) funded by the Ministry of Science, ICT & Future Planning, Republic of Korea.

TECHNICAL FIELD

The present invention relates to a method of preparing vascular endothelial cells by transforming (transdifferentiating) adult fibroblasts and a method of treating ischemic diseases by transdifferentiating.

BACKGROUND ART

Angiogenesis is a highly regulated process occurring due to reactions to various angiogenic factors, such as hypoxia and low pH, as well as growth factors, cytokines, and other physiological molecules (Folkman and Shing, J. Biol. Chem., 267, 10931, 1992). To develop new blood vessels, the angiogenesis mechanism requires cooperation with various molecules that regulate decomposition and reconstruction, migration, proliferation, differentiation, and tube-formation of extra-the cellular matrix (ECM). In addition, after the initiation of angiogenesis, angiogenesis promotion factors including VEGF, bFGF, PDGF, etc. activate by stimulating receptors on cell surfaces. The activated cells induce cellular proliferation, the expression of cell adhesion molecules, the secretion of proteolytic enzymes, and cellular migration and infiltration. In addition, various molecules including integrins for cell adhesion, selectin, immunoglobulin gene superfamily members, and enzymes for protein decomposition, such as matrix metaloprotease for ECM decomposition and serine protease promote the proliferation and infiltration of cells (Brooks, Eur. J. Cancer, 32A, 2423, 1996), Further, lumen formation and differentiation to mature blood vessels are induced by a signal transduction mechanism mediated by the cell surface receptor that can interact with ECM components and lytic factors, resulting in angiogenesis.

Recently, attempts have been actively made to treat angiogenesis-mediated diseases such as cancer, rheumatoid arthritis, psoriasis, ulcer, ischemia, atherosclerosis, myocardial infarction, angina pectoris, and cerebrovascular disease, using a factor that induces or inhibits angiogenesis (Folkman J., J. Nat. Med., 1:27, 1995; Jackson J. R., et al., FASEB J., 11:457, 1997; Risau W., Nature, 386:671, 1997; Bussolino, F., et al., Trends Biochem. Sci., 22:251, 1997; Hanahan D., et al., Cell, 86:353, 1996).

In normal adults, endothelial cells composing blood vessels are replaced every 47 to 20,000 days, which is strictly regulated. In general, angiogenesis inhibitors, such as thrombospondin-1, platelet factor-4, and angiostatin, and the angiogenesis promoters, such as vascular endothelial growth factor (VEGF) and basic fibroblast growth factor (bFGF), are quantitatively balanced, whereby angiogenesis is not induced. However, when a wound or cancer is developed, the balance between angiogenesis inhibitors and angiogenesis promoters is broken in order to induce regeneration of wounded tissue and growth of cancer and new blood vessels are formed. In this case, over-expression of angiogenesis promoters is induced.

Accordingly, excessive blood vessel formation can be a major cause of disease exacerbation and non-formation of the blood vessels can also be a cause of severe diseases. Angiogenesis is considered to be an essential phenomenon for wound healing or tissue regeneration. For example, a lack of angiogenesis in the placenta can be a major cause of miscarriages. In addition, necrosis, ulcer, and ischemia due to a lack of angiogenesis may cause dysfunction in tissues or organs or even death.

Therefore, it is very important to induce or promote formation of new vessels so as to reduce tissue damage caused by a hypoxic or mal-nutrition state due to non-formation of blood vessels and to induce smooth tissue regeneration.

In particular, a wound repair process essential for regeneration of wounded skin tissue should be necessarily accompanied by angiogenesis. In the early stage of wound repair, inflammation occurs due to cellular necrosis and blood vessel destruction. After such inflammation, a series of processes such as formation of biological mediators, such as kallikrein, thrombin, and plasmin, along with the escape of blood components, platelet activation, blood coagulation followed.

Ischemia is a partial blood shortage symptom wherein normal angiogenesis is not sufficiently performed and thus blood supply is stopped, whereby cell damage is caused. Ischemic diseases is a generic term including all diseases induced by such ischemia. For example, examples of ischemic diseases include lower limb ischemia, ischemic stroke, ischemic colitis and cardiovascular diseases. In the case of ischemic stroke or ischemic heart disease, as a representative ischemic diseases, brain cells and cardiocytes are damaged by ischemia wherein cerebral arteries or coronary arteries are obstructed by a thrombus or arteriosclerosis and a blood flow rate is decreased to a threshold or lower, and finally cellular necrosis occurs, whereby cerebral infarction and myocardial infarction occur. A blood supply shortage due to ischemia also causes various ischemic diseases such as ischemic heart failure, ischemic enteritis, ocular disease, and lower limb ischemia.

As methods of treating such ischemic diseases, there are a pharmacotherapy method and a coronary angioplasty method of distending narrow blood vessels by means of a stent. In the case of the heart, artery bypass surgery may be conducted. However, such treatments are not suitable methods when blood vessels are extremely hardened, all blood vessels available for transplantation were used, or relapsing continues despite repeated arterioplasty by restenosis. Therefore, to overcome the limitations of such operative treatments, research on a method of treating ischemic diseases characterized by directly injecting vascular endothelial cells into tissue and thus allowing new blood vessels to be formed in a damaged region is underway.

Angiogenesis with vascular endothelial cells has great clinical significance with regard to ischemic blood vessel diseases. However, when vascular endothelial cells derived from different species are injected, problems related with biocompatibility may occur. To address such problems, attempts to derive autologous vascular endothelial cells from embryonic stem cells or induced pluripotent stem cells are being made. However, a defined differentiation method does not yet exist and limitations due to technically difficult embryoid body manipulation, low differentiation efficiency, contamination possibility by feeder cells, etc. are present. To overcome such limitations, a method of directly transdifferentiating differentiated cells into a different cell type is actively underway. With regard to this, it was reported that it was possible to transdifferentiate beta cells of the pancreas, nerve cells, cardiac myocytes, hepatocytes, etc. In 2012, Ginsberg et al. showed that, by introducing ER71, FLI1, and ERG1 into human amnion cells and inhibiting TGFβ, the human amnion cells were transdifferentiated into endothelial cells.

However, Ginsberg et al. failed to transdifferentiate adult cells into endothelial cells. They only accomplished transdifferentiation of amniotic cells. Their study has limited clinical relevance because amniotic cells are not readily available and because this approach still possesses the critical limitations of embryonic stem cells-derived ECs such as immunogenicity and possible allograft rejection. Moreover, amniotic cells isolated from amniotic fluid of midgestation human fetuses should be distinct from fully differentiated mature cells. Thus, the clinical application of their study is quite limited.

DISCLOSURE

Technical Problem

Therefore, the present invention has been made in view of the above problems. The present inventors confirmed that five factors, which are Foxo1, Er71, Klf2, Tal1, and Lmo2, or three factors, which are Er71, Klf2, and Tal1 induce transformation (transdifferentiation) of adult fibroblasts into endothelial cells and the resultant induced endothelial cells enable lower limb salvaging by angiogenesis in lower limb ischemia models. The present invention suggests that vascular endothelial cells prepared according to a method of the present invention can be applied to a novel treatment method of treating ischemic diseases.

It will be understood that technical problems of the present invention are not limited to the aforementioned problems and other technical problems not referred to herein will be clearly understood by those skilled in the art from disclosures below.

Technical Solution

In accordance with an aspect of the present invention, the above and other objects can be accomplished by the provision of a method of preparing vascular endothelial cells by transdifferentiating target cells, the method including a step of transducing target cells with genes, wherein the genes comprise Er71 and Klf2.

In an embodiment of the present invention, the genes may further include Tal1 gene.

In another embodiment of the present invention, the genes may further include Foxo1 gene.

In another embodiment of the present invention, the genes may further include Tal1 or LMO2 gene.

In another embodiment of the present invention, the genes may further include Tal1 and LMO2 genes.

In another embodiment of the present invention, the target cells may be adult fibroblasts.

In another embodiment of the present invention, the adult fibroblasts may be skin fibroblasts (SFBs) or tail-tip fibroblasts (TTFs).

In another embodiment of the present invention, the Foxo1 gene may be NM_019739 as an NCBI Accession number.

In another embodiment of the present invention, the Er71 gene may be NM_007959 as an NCBI Accession number.

In another embodiment of the present invention, the Klf2 gene may be NM_008452 as an NCBI Accession number.

In another embodiment of the present invention, the Tal1 gene may be NM_011527 as an NCBI Accession number.

In another embodiment of the present invention, the LMO2 gene may be BC057880 as an NCBI Accession number.

In addition, the present invention provides a composition for preventing or treating ischemic diseases, including vascular endothelial cells, as an effective ingredient, transdifferentiated from adult fibroblasts according to the method.

In an embodiment of the present invention, the adult fibroblasts may be skin fibroblasts (SFBs) or tail-tip fibroblasts (TTFs).

In another embodiment of the present invention, ischemic diseases may be selected from lower limb ischemia, ischemic brain disease, ischemic cerebrovascular disease, and ischemic heart disease.

In still another embodiment of the present invention, the lower limb ischemia may be selected from the group consisting of lower limb arterial occlusive disease, lower limb arterial stenosis, and lower limb arteriosclerosis.

In yet another embodiment of the present invention, the ischemic heart disease may be selected from the group consisting of coronary artery disease, angina, myocardial infarct, congestive heart failure, chronic heart failure, cardiomyopathy, and myocardial infarction.

In yet another embodiment of the present invention, the cardiomyopathy may be selected from the group consisting of ischemic cardiomyopathy, dilated cardiomyopathy, hypertrophic cardiomyopathy, idiopathic cardiomyopathy, primary cardiomyopathy, secondary cardiomyopathy, and valvular cardiomyopathy.

Advantageous Effects

Vascular endothelial cells transdifferentiated from adult fibroblasts according to a method of the present invention have a shape similar to real vascular endothelial cells, function as endothelial cells, and exhibit genetic and epigenetic profiles of the real endothelial cells. In addition, when the transdifferentiated vascular endothelial cells are injected into mouse and human hind/lower limb ischemia models, lower limb salvage effects by angiogenesis are exhibited and thus the transdifferentiated vascular endothelial cells can be useful for ischemic disease treatment.

In addition, the present invention first confirms that adult fibroblast can be transdifferentiated into vascular endothelial cells by using defined factors and provides an important evidence suggesting that differentiation during embryonic development is not an irreversible phenomenon, and the destiny of the cells can go back to a primitive and pluripotent stage and also directly proceed to all other lineages through configuration of a new transcriptional network. Further, the present invention suggests a novel treatment method to overcome limitations in applying endothelial cells, which are derived from embryonic stem cells or induced pluripotent stem cells, to clinical trials.

DESCRIPTION OF DRAWINGS

FIG. 1 illustrates the distribution of GFP⁻ cells in skin fibroblasts isolated from Tie2-GFP mice.

FIG. 2 illustrates the percentage of GFP⁺ cells generated by transducing Tie2-GFP⁻ cells with lentivirus expressing 11 factors considered as key regulators of vascular endothelial development.

FIG. 3 illustrates the percentages of GFP⁺ cells generated by transducing Tie2-GFP⁻ cells with lentivirus expressing each of 11 factors.

FIG. 4 illustrates the percentages of GFP⁺ cells generated by transducing Tie2-GFP⁻ cells with lentivirus expressing each of the factors, in addition to two factors, Foxo1 and Er71.

FIG. 5 illustrates the percentages of GFP⁺ cells generated by transducing Tie2-GFP⁻ cells with lentivirus expressing each of the factors, in addition to three factors, Foxo1, Er71, and Klf2.

FIG. 6 illustrates the percentages of GFP⁺ cells generated by transducing Tie2-GFP⁻ cells with lentivirus expressing each of the factors, in addition to four factors, Foxo1, Er71, Klf2, and Tal1.

FIG. 7 illustrates the percentages of GFP⁺ cells generated by adding any single factor in addition to five factors, Foxo1, Er71, Klf2, Tal1, and Lmo2 (a), or by eliminating one of the five factors.

FIG. 8 illustrates an experimental design to transdifferentiate adult skin fibroblasts into vascular endothelial cells using the five factors.

FIG. 9 illustrates the percentage of GFP⁺ cells generated by transducing adult skin fibroblasts with the five factors.

FIG. 10 illustrates the shapes of cells generated by transducing adult skin fibroblasts using the five factors.

FIG. 11 illustrates an experimental design to transdifferentiate adult tail-tip fibroblasts into vascular endothelial cells using the five factors.

FIG. 12 illustrates the percentage of GFP⁺ cells generated by transducing adult tail-tip fibroblasts with the five factors.

FIG. 13 illustrates the shapes of cells generated by transducing adult tail-tip fibroblasts with the five factors.

FIG. 14 illustrates the shapes of Tie2-GFP⁺ cells transduced with the 5F factors and then isolated and cultured.

FIG. 15 illustrates comparison results of relative mRNA expressions of vascular endothelium-specific genes in induced endothelial cells of the present invention and other cell types (SFBs, primary ECs, and MS1).

FIG. 16 illustrates immunofluorescence staining results performed to investigate the binding affinity of BS1 lectin in induced endothelial cells of the present invention and other cell types (SFBs, primary ECs, and MS1).

FIG. 17 illustrates immunofluorescence staining results to investigate Ac-LDL uptake in induced endothelial cells of the present invention and other cell types (SFBs, primary ECs, and MS1).

FIG. 18 illustrates that induced endothelial cells of the present invention form capillary tubes on Matrigel.

FIG. 19 illustrates NO production amounts of induced endothelial cells of the present invention and other cell types (SFBs, primary ECs, and MS1).

FIG. 20 illustrates bisulfite genomic sequencing results of induced endothelial cells of the present invention and other cell types (SFBs, primary ECs, and MS1).

FIG. 21 illustrates global gene expression profile clustering results of microarrays prepared using induced endothelial cells of the present invention and other cell types (SFBs, primary ECs, and MS1).

FIG. 22 illustrates EC-specific gene expression comparison results, by gene ontology, of microarrays prepared using induced endothelial cells of the present invention and other cell types (SFBs, primary ECs, and MS1).

FIG. 23 illustrates expression comparison results of genes related to EC development, by gene ontology, in microarrays prepared using induced endothelial cells of the present invention and other cell types (SFBs, primary ECs, and MS1).

FIG. 24 illustrates expression comparison results of genes related to EC morphogenesis, by gene ontology, in microarrays prepared using induced endothelial cells of the present invention and other cell types (SFBs, primary ECs, and MS1).

FIG. 25 illustrates expression comparison results of genes related to EC differentiation, by gene ontology, in microarrays prepared using induced endothelial cells of the present invention and other cell types (SFBs, primary ECs, and MS1).

FIG. 26 illustrates expression comparison results of genes related to vascular endothelium development, by gene ontology, in microarrays prepared using induced endothelial cells of the present invention and other cell types (SFBs, primary ECs, and MS1).

FIG. 27 illustrates expression comparison results of genes related to EC migration control, by gene ontology, in microarrays prepared using induced endothelial cells of the present invention and other cell types (SFBs, primary ECs, and MS1).

FIG. 28 illustrates that, although six factors, except for 5F, of 11 factors, as key regulators of vascular endothelial development, are not transduced by lentivirus, the six factors are satisfactorily expressed at gene level.

FIG. 29 illustrates the shapes and GFP⁺ cell percentage of Tie2-GFP⁻ cells transduced with lentivirus expressing three ETS family factors.

FIG. 30 illustrates that induced endothelial cells of the present invention are not involved in activation of pluripotency when applied to Oct4 promoter-driven GFP mice.

FIG. 31 illustrates that induced endothelial cells of the present invention do not involve in activation of pluripotency when applied to Nanog promoter-driven GFP mice FIG. 32 illustrates treatment effects by assessing lower limb morphologies (a), LDPI images (b), LDPI quantification results (c) of lower limb ischemic animal models injected with induced endothelial cells of the present invention and other cell types (SFBs, primary ECs, and MS1).

FIG. 33 illustrates quantification results of capillary densities of lower limb ischemic animal models injected with induced endothelial cells of the present invention and other cell types (SFBs, primary ECs, and MS1).

FIG. 34 illustrates capillary densities, observed by immunofluorescence staining, in lower limb ischemic animal models injected with induced endothelial cells of the present invention and other cell types (SFBs, primary ECs, and MS1).

FIG. 35 illustrates a cell-injected region, observed by immunostaining, in a lower limb ischemic animal model injected with induced endothelial cells of the present invention.

FIG. 36 illustrates vascular endothelial cells transdifferentiated from human fibroblasts.

FIG. 37 illustrates the shapes of human fibroblasts transduced with three factors.

FIG. 38 illustrates immunofluorescence staining results to investigate Ac-LDL uptake in induced human endothelial cells of the present invention and other cell types (HUVEC).

FIG. 39 illustrates that induced human endothelial cells of the present invention form capillary tubes on Matrigel.

FIG. 40 illustrates NO production amounts of induced human endothelial cells of the present invention and other cell types (HUVEC and GEAEC).

FIG. 41 illustrates the shapes of induced human endothelial cells of the present invention and other cell types (HUVEC and GEAEC).

MODES OF THE INVENTION

The present inventors performed research on factors that can induce transdifferentiation of target cells into vascular endothelial cells. As a result, the present inventors confirmed that five factors, Foxo1, Er71, Klf2, Tal1, and Lmo2, induce transdifferentiation of adult fibroblasts into induced endothelial cells. Furthermore, the present inventors confirmed that three factors, Er71, Klf2, and Tal1, induce transdifferentiation of human adult fibroblasts into induced endothelial cells. The resultant induced endothelial cells enable lower limb salvaging by angiogenesis in lower limb ischemia models, suggesting that the induced endothelial cells also function in vivo. The present invention can be clinically applied in two different ways as follows. The vascular endothelial cells prepared according to a method of the present invention can be administered to ischemic tissue or organs. Or the defined genetic factors according to the present invention can be directly administered to ischemic tissue or organs to make endothelial cells in vivo.

Hereinafter, the present invention will be described in detail.

To accomplish the aforementioned objects, the present invention includes a method of preparing vascular endothelial cells by transdifferentiating target cells, the method including a step of transducing target cells with a gene, wherein the gene includes Er71 and Klf2.

Preferably, the target cells may be adult fibroblasts.

In addition to this, the gene may further include Tal1 or Foxo1.

In addition to this, the gene preferably further includes Tal1 or LMO2, or Tal1 and LMO2, but the present invention is not limited thereto. It was confirmed that, when mouse adult fibroblasts are transduced with Foxo1, Er71, and Klf2 genes as in the following examples, the adult fibroblasts was transdifferentiated into endothelial cells. When Tal1 and Lmo2 are added to the combination of Foxo1, Er71, and Klf2, the efficiency of transdifferentiation is improved. Furthermore, it was confirmed that, when human cells are transdifferentiated into endothelial cells, transduction with the combination of Er71, Klf2, and Tal1 is ideal. The adult fibroblasts are preferably skin fibroblasts (SFBs) or tail-tip fibroblasts (TTFs), but the present invention is not limited thereto.

The Foxo1 gene is preferably NM_019739 as an NCBI Accession number, but the present invention is not limited thereto.

The Er71 gene is preferably NM_007959 as an NCBI Accession number, but the present invention is not limited thereto.

The Klf2 gene is preferably NM_008452 as an NCBI Accession number, but the present invention is not limited thereto.

The Tal1 gene is preferably NM_011527 as an NCBI Accession number, but the present invention is not limited thereto.

The LMO2 gene is preferably BC057880 as an NCBI Accession number, but the present invention is not limited thereto.

In addition, the present invention provides a composition for preventing or treating ischemic diseases, including vascular endothelial cells transdifferentiated from adult fibroblasts or the defined genetic factor combination themselves, as effective ingredients. In addition to this, the present invention provides a method of treating ischemic diseases, the method including a step of administering vascular endothelial cells prepared by the method, or a step of transduction of cells in vivo by administration of the specific genes themselves.

The adult fibroblasts are preferably skin fibroblasts (SFBs) or tail-tip fibroblasts (TTFs), but the present invention is not limited thereto.

In the present invention, the term "composition for preventing or treating ischemic diseases" refers to a composition including vascular endothelial cells prepared by the method, or the defined genetic factor combination themselves Examples of ischemic diseases include lower limb ischemia, ischemic cerebrovascular disease or ischemic heart disease, but the present invention is not limited thereto. Lower limb ischemia includes lower limb arterial occlusive disease, lower limb arterial stenosis, and lower limb arteriosclerosis, but the present invention is not limited thereto.

In addition, the ischemic cerebrovascular disease includes stroke and cerebrovascular dementia, but the present invention is not limited thereto.

In addition, examples of the ischemic heart disease include coronary artery disease, congestive heart failure, chronic heart failure, cardiomyopathy and myocardial infarction, but the present invention is not limited thereto. The cardiomyopathy refers to various diseases typified by heart muscle disorder characterized by dyspnea, chest pain, palpitation, etc., without heart diseases such as congenital heart disease, valvular disease, hypertension, coronary disease, pericardial disease. Examples of the cardiomyopathy include ischemic cardiomyopathy, dilated cardiomyopathy, hypertrophic cardiomyopathy, idiopathic cardiomyopathy, primary cardiomyopathy, secondary cardiomyopathy, and valvular cardiomyopathy, but the present invention is not limited thereto.

Ischemic diseases can be treated by administering or transplanting the composition for preventing or treating ischemic diseases according to the present invention into the tissue of a live animal subject, thereby promoting new blood vessel formation, The composition of the present invention may include, in addition to effective ingredients, a general pharmaceutically acceptable carrier. When the composition is a formulation for injection, a preservative, an agent for relieving pain upon injection, a solubilizer, a stabilizer, etc. may be included. When the composition is a formulation for topical administration, a base, a vehicle, a lubricant, a preservative, etc. may be included.

The pharmaceutically acceptable carrier included in the composition of the present invention may include generally used lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, mineral oil, etc., but the present invention is not limited thereto. The composition of the present invention may further include, in addition to the ingredient, a lubricant, a wetting agent, a sweetener, a flavor, an emulsifier, a suspension, a preservative, etc.

According to a method easily performed by those skilled in the art, the composition of the present invention may be formulated using a pharmaceutically acceptable carrier and/or an excipient so as to be prepared in a unit dosage form or contained in a container including multiple unit doses. Here, a prepared formulation may be a solution in an oily or aqueous medium, a suspension, or an emulsion and further include a dispersant or a stabilizer.

The composition according to the present invention may be administered to humans and animals via oral or parenteral administration such as intravenous injection, subcutaneous injection, intranasal administration, or intraperitoneal injection. The oral administration includes sublingual administration. The parenteral administration includes administration by injection, such as subcutaneous injection, intramuscular injection, or intravenous injection, and drips. Such administration methods may be applied to any tissue, cellular necrosis of which is induced by ischemia. Preferably, the administration may be performed by intramuscular injection. A composition for parenteral administration (e.g., formulation for injection) according to the present invention may be administered into the body after being dispersed and/or dissolved in a pharmaceutically acceptable carrier, such as, for example, sterile purified water, a buffer having pH about 7, or a saline solution. As needed, a general additive such as a preservative or a stabilizer may be included.

In addition, the amount of the induced endothelial cells injected according to the present invention is not greatly limited, but the induced endothelial cells may be injected in an amount of $1\times10^2$ to $1\times10^6$ cells per injection, preferably, $1\times10^3$ to $5\times10^5$ cells per injection, most preferably, $5\times10^5$ cells per injection, but the present invention is not limited thereto. The amount may be varied depending upon various factors such as a formulation method, an administration manner, the age, weight, sex, and condition of a patient, food, administration time, an administration route, an excretion rate, and sensitivity to reaction.

In the present invention, the term "prevention" refers to all actions that inhibit ischemic diseases or delay the development thereof by administering the composition of the present invention.

In the present invention, the term "treatment" refers to 1) prevention of the development of a disease or disorder in an animal, preferably, a mammal, more preferably, human, not having ischemic diseases yet but showing the possibility of ischemic diseases, 2) inhibition of ischemic diseases, i.e., inhibition of the development of ischemic diseases, and 3) alleviation of ischemic diseases. In particular, when a therapeutically effective amount of the composition is injected into a damaged tissue of a subject with ischemic diseases in need of treatment, neighboring fibroblasts are differentiated into vascular endothelial cells and thus new blood vessels are formed, whereby the functionality of the damaged tissue can be recovered and ischemic diseases can be treated. Meanwhile, the administered subject may be a mammal including humans.

In the present specification, terms have meanings generally used in the art, unless specified otherwise.

When the composition of the present invention is used to prevent or treat ischemic diseases, the composition of the present invention may be used alone or in a combination with conventional chemotherapy or physical surgery or intervention. When such a combined treatment is performed, ischemic diseases may be more effectively treated.

Now, the present invention will be described in more detail with reference to the following preferred examples. These examples are provided for illustrative purposes only and should not be construed as limiting the scope and spirit of the present invention.

EXAMPLES

Example 1

Selection of Factors for Inducing Transdifferentiation of Adult Fibroblasts into Vascular Endothelial Cells The present inventors conducted the following experiments to select optimal factors for inducing transdifferentiation of adult fibroblasts into vascular endothelial cells.

1-1. Selection of 11 Candidate Genes and Production of Lentivirus for Gene Expression The present inventors selected 11 genes which are considered to be key regulators of vascular endothelial development (Table 1), and produced lentivirus for expressing each of the selected genes.

TABLE 1

| Gene symbol | NCBI Accession number |
|---|---|
| Gata2 | NM_008090 |
| Foxc2 | NM_013519 |
| Elf1 | NM_007920 |
| Erg | NM_133659 |
| Fli1 | NM_008026 |
| Tal1 | NM_011527 |
| Foxo1 | NM_019739 |
| Lmo2 | BC057880 |
| Ets1 | BC010588 |
| Er71 | NM_007959 |
| Klf2 | NM_008452 |

In particular, a coding sequence of each gene was amplified by RT-PCR and subcloned into pENTR1A entry vectors (Invitrogen) to create entry clones. Mouse Er71 cDNA was provided by S. Sumanas, mouse Fli1 and Elf1 cDNAs by B. Göttgens, mouse Gata2 and Erg cDNAs by P. Oettgen. LR recombination reaction was performed for insertion into a pLenti6.3/V5-DEST destination vector (Invitrogen). pLenti6.3N5-GW/lacZ (Invitrogen) was used as a mock vector.

To produce lentivirus, plasmids for destination vectors, pLP1, pLP2, and pLP/VSVG (Invitrogen) (10 μg for each plasmid) were mixed with 1 mg/ml polyethylenimine (Polysciences), followed by being introduced into 293T cells. 1 day after incubation at 37° C. under 5% $CO_2$, the medium was replaced with fresh DMEM with 10% FBS. A culture supernatant was collected 20 hours after the medium change. After filtration through a 0.45 μm strainer, a viral supernatant was concentrated by centrifugation (25,000 rpm for 1.5 hours at 4° C.). The viral pellets were resuspended in DMEM.

1-2. Isolation of Adult Skin Fibroblasts

Skin fibroblasts (SFBs) to be differentiation-induced into vascular endothelial cells were prepared from transgenic mice (Tie2-GFP) expressing Tie2 promoter-driven green fluorescent protein (GFP).

In particular, a skin fragment of 8 week old male Tie2 promoter-driven GFP mice (FVB/N background, Jackson Laboratory) was peeled off in one piece using surgical scissors. After the removal of fat, dermis was separated from epidermis by a pair of sterile forceps. The dermis was washed three times with phosphate-buffered saline (PBS), and sliced into 4 to 5 pieces. The pieces were incubated in DMEM (Gibco) with 0.1% collagenase (Gibco) on a 35 mm petri-dish (SPL) for 1.5 hours at 37° C. under 5% $CO_2$. Next, the tissue fragments were rinsed three times with PBS, and treated with 0.25% trypsin (Gibco) for 20 min. Cells were collected by centrifugation (1300 rpm for 7 min at 4° C.), resuspended in DMEM containing 10% FBS (Gibco), penicillin/streptomycin (Gibco), L-Glutamine (Gibco), and sodium pyruvate (Gibco), and seeded on 0.1% gelatin-coated 6 well plates (Nunc). After culturing for 5 days, $GFP^-$ cells were sorted using FACS. For the FACS, FACS Aria™II (BD) was used and data was analyzed using FACS Diva software (version 6.1.3).

As a result, all skin fibroblasts (100%) isolated from Tie2-GFP mice (SFBs) were not observed to not have GFP fluorescence which is observed in vascular endothelial cells (FIG. 1). From this data, it can be confirmed that the skin fibroblasts isolated according to the present invention do not include vascular endothelial cells at all.

1-3. Infection of Adult Skin Fibroblasts with Lentivirus

The $GFP^-$ target cells confirmed in Example 1-2 were cultured in DMEM with lentivirus expressing 11 factors prepared according to Example 1-1 and 10 mg/ml of Polybrene. By such culturing, the cells were infected with the lentivirus. After allowing infection for 24 hours, the medium containing the lentivirus was replaced with fresh DMEM containing 10% FBS and penicillin/streptomycin. After 24 hours, the medium was replaced with EBM-2 containing 10% FBS and penicillin/streptomycin again. 12 days after the viral infection, cells were harvested and subjected to a FACS analysis using the same method as in Example 1-2.

As a result, it was confirmed that, after infecting the target cells, $GFP^+$ cells which were not observed before, with the virus, a small percent, i.e., 0.9%, of $GFP^+$ cells was observed. From this data, it can be confirmed that the Tie2 gene specific to vascular endothelial cells can be activated in adult fibroblasts by the defined factors (FIG. 2).

Example 2

Selection of Five Factors Suitable for Inducing Trans Differentiation of Adult Fibroblasts into Vascular Endothelial Cells To investigate whether the 11 factors confirmed in Example 1 were essential to activate the vascular endothelium-specific gene, lentivirus expressing each of the factors was transduced into adult skin fibroblasts.

As a result, it was confirmed that, only when Foxo1 and Er71 were transduced, Tie2-$GFP^+$ cells were generated (FIG. 3). In addition, it was confirmed that, when Foxo1 and Er71 were combined, the percentage of $GFP^+$ cells was increased to 0.6%. In addition to the two factors, transduction with each factor was continuously performed. As a result, it was confirmed that, when, in addition to the two factors (Foxo1 and Er71), the Klf2 factor was transduced, the proportion of $GFP^+$ cells remarkably increases (FIG. 4).

In addition, it was confirmed that the proportion of $GFP^+$ cells further increased when, in addition to three factors (Foxo1, Er71, and Klf2), the Tal1 factor was transduced (FIG. 5), and the proportion of $GFP^+$ cells increased the most when, in addition to four factors (Foxo1, Er71, Klf2, and Tal1), the Lmo2 factor was transduced (FIG. 6).

Further, it was confirmed that the proportion of $GFP^+$ cells was decreased when another factor, in addition to the five factors (Foxo1, Er71, Klf2, Tal1, and Lmo2), was additionally transduced (FIG. 7a) or one of the five factors (FIG. 7b) was eliminated (FIG. 7). From this data, it can be confirmed that the combination of the five factors is the most effective and essential combination to induce differentiation of the adult fibroblasts into $GFP^+$ vascular endothelial cells.

Example 3

Induction of Differentiation of Vascular Endothelial Cells Using Five Selected Differentiation Induction Factors 3-1. Induction of Differentiation of Adult Skin Fibroblasts (SFBs) into Vascular Endothelial Cells To reconfirm whether the combination of the five differentiation induction factors (Foxo1, Er71, Klf2, Tal1, and Lmo2: 5F) confirmed in Example 2 induced transdifferentiation of adult skin fibroblasts into vascular endothelial cells, an experiment was conducted according to a method illustrated in FIG. 8.

As a result, it was confirmed that, when the adult skin fibroblasts was transduced with 5F, the activation of the Tie2 promoter was induced in 4.0% of SFBs (FIG. 9) and the resultant cells had a cobblestone shape similar to the shape of vascular endothelial cells (FIG. 10).

3-2. Induction of Differentiation of Adult Tail-Tip Fibroblasts (TTFs) into Vascular Endothelial Cells In addition, to investigate whether 5F exhibited the same differentiation induction effects in fibroblasts derived from a different adult tissue, mouse tail-tip fibroblasts (TTFs) were used.

First, tails of 8 week old Tie2 promoter-driven GFP mice (FVB/N background, Jackson Laboratory) were cut. Superficial dermis was peeled off by hand, and the remaining tail was cut into 1 cm pieces with scissors. The pieces were placed on 0.1% gelatin-coated 6 well plates, and cultured in DMEM supplemented with 20% FBS, penicillin/streptomycin, L-Glutamine and Sodium Pyruvate. After attachment, fibroblasts migrated out of the tail explants. After culturing for 5 days, the explants were removed and discarded. When the cells were cultured to confluence, $GFP^-$ cells were sorted using FACS, thereby obtaining pure TTFs. Subsequently, isolated TTFs were transduced with 5F (retrovirus) according to a method illustrated in FIG. 11. It was investigated whether differentiation of the transduced TTFs into vascular endothelial cells was induced.

As a result, it was confirmed that, when the adult tail-tip fibroblasts were transduced with 5F, activation of the Tie2 promoter was induced in 5.4% of TTFs (FIG. 12) and the resultant cells had a cobblestone shape similar to the shape of vascular endothelial cells (FIG. 13).

Form this data, it can be confirmed that the selected 5F (Foxo1, Er71, Klf2, Tal1, Lmo2) of the present invention have the same differentiation induction effect on fibroblasts derived from various adult tissues.

Example 4

Analysis of Characteristics of Induced Vascular Endothelial Cells of the Present Invention It was confirmed that, when Tie2-$GFP^+$ cells obtained after being transduced with 5F were isolated and cultured, the cells also had a cobblestone shape similar to the shape of vascular endothelial cells (FIG. 14). These induced vascular endothelial cells were named iECs and endothelial functions thereof were analyzed.

4-1. Quantitative Real Time PCR Analysis

First, to compare mRNA expression patterns of CD31, VE-cadherin, ICAM2, and Tie2, as intracellular vascular endothelium-specific genes, quantitative real time PCR was conducted.

In particular, Total RNA was isolated using the RNeasy Mini Kit (Qiagen) and cDNA was obtained with the amfiRivert cDNA Synthesis Premix (GenDEPOT). Quantitative real-time PCR was performed with Power SYBR Green (Applied Biosystems) on the 7500 Real-Time PCR System (Applied Biosystems). 18S rRNA was used to normalize samples. Primer sequences are provided in Table 2 below.

TABLE 2

| Gene symbol | Accession No. | Primer sequence | Sense/antisense | Usage |
|---|---|---|---|---|
| CD31 | NM_008452 | gcccaatcacgtttcagttt | Sense | Real-time |
|  |  | aaaacgcttgggtgtcattc | Antisense | Real-time |
| VE-cadherin | NM_009868 | atcgccaaaagagagactgg | Sense | Real-time |
|  |  | gcaaactctccttggagcac | Antisense | Real-time |
| ICAM2 | NM_010494 | catcctcaagggaagtggaa | Sense | Real-time |
|  |  | acttgagctggaggctggta | Antisense | Real-time |
| Tie2 | NM_013690 | ccctcctcaaccagaaaaca | Sense | Real-time |
|  |  | ttgccctgaaccttataccg | Antisense | Real-time |
| 18S rRNA | NR_003278 | gtaacccgttgaaccccatt | Sense | Real-time |
|  |  | ccatccaatcggtagtagcg | Antisense | Real-time |
| VE-cadherin | NM_009868 | ttgaggtatgagttgaatatttta | Sense | Methylation |
|  |  | ttatatccttacacactaaaaaatata | Antisense | Methylation |
| Tie2 | NM_013690 | ttgtaaaggaaataggaaaaaggaat | Sense | Methylation |
|  |  | tccacaaataaacataaatccctaaa | Antisense | Methylation |

Here, as positive controls, primary vascular endothelial cells (primary EC) and Mile Sven 1 (MS1) were used.

Primary vascular endothelial cells were isolated form 8 week old Tie2 promoter-driven GFP mouse lungs (FVB/N background, Jackson Laboratory). In particular, lungs were excised after systemic perfusion with PBS to remove blood. Lung tissue was minced well with a sterile razor, and incubated with a prewarmed digestion buffer containing DMEM, 1 mg/ml collagenase I (Worthington), 1 mg/ml collagenase II (Gibco), 10 mg/ml bovine serum albumin (Amresco), and 1 U/ml dispase (Gibco) at 37° C. under 5% $CO_2$ with stirring every 10 minutes. After 30 minutes, 1/10 volume of FBS was added to the buffer. Cells were filtered through a 70 μm cell strainer, and incubated on a 10 cm culture dish at 37° C. under 5% $CO_2$. 1 hour after incubation, nonattached cells were collected, and double positive cells for Tie2-GFP and CD31 were sorted by FACS. Finally isolated primary ECs were cultured in EBM-2 with 10% FBS and penicillin/streptomycin on 1.5% gelatin-coated plates.

Mile Sven1 (MS1) is SV40 transformed pancreatic islet vascular endothelial cell line (ATCC CRL-2279).

As a result, it was confirmed that mRNA expressions of CD31, VE-cadherin, ICAM2 and Tie2 genes in the induced vascular endothelial cells were remarkably increased compared to the adult skin fibroblasts, as a negative control (FIG. 15). ICAM2 expression in the induced vascular endothelial cells was very small compared to MS1, but was comparable to the mouse lung-derived primary ECs.

4-2. Immunofluorescence Staining

The same result was confirmed by immunofluorescence staining (FIG. 16). The induced vascular endothelial cells of the present invention possessed endothelial characteristics such *Bandeiraea simplicifolia* (BS)1 lectin binding, and acetylated-low density lipoprotein (Ac-LDL) uptake (FIG. 17).

A particular experimental method therefor is as follows.

To perform immunofluorescence staining, cells were fixed with 1% paraformaldehyde for 10 minutes at room temperature. After washing with TBS-T (Amresco) and blocking with PBS containing 1% BSA, cells were incubated with primary antibodies against goat VE-cadherin (1:100, Santa Cruz Biotechnology), goat CD31 (1:100, Santa Cruz Biotechnology), and TRITC-conjugated BS1-lectin (1:20000, Sigma-Aldrich). After overnight incubation at 4° C., culture plates were washed with TBS-T, and incubated with an Alexa Fluor 555 donkey anti-goat IgG (1:100, Invitrogen) secondary antibody (for VE-cadherin, CD31) for one hour at room temperature. DAPI was used for nuclei staining. Fluorescence images were taken using an LSM 710 fluorescence microscope (Zeiss).

To investigate DiI-Ac-LDL uptake, after incubation with 10 μg/ml DiI-Ac-LDL (Invitrogen) for 12 hours at 37° C. under 5% $CO_2$, cells were stained with DAPI. To detect Di1-Ac-LDL uptake, cells were imaged using an LSM 710 fluorescence microscope.

4-3. Matrigel Tube Formation and NO Generation

In addition, it was confirmed that induced vascular endothelial cells of the present invention were formed into capillary tubes on Matrigel, similarly to the primary vascular endothelial cells or MS1 (FIG. 18) and can produce nitric oxide (NO), as an important factor for the functionality of blood vessels, in an amount equal to that produced by the primary vascular endothelial cells or MS1 (FIG. 19).

A particular experimental method therefor is as follows.

To allow Matrigel tube formation, Matrigel Matrix (BD) was coated on culture plates and incubated at 37° C. for 30 minutes. Subsequently, $4 \times 10^4$ cells were seeded on the plates. After incubation at 37° C. under 5% $CO_2$ for 9 hours, tube formation was analyzed using an IX71 microscope (Olympus).

To investigate NO generation, 3×10⁴ cells were seeded on a 1.5% gelatin-coated culture dish, and cultured in EBM-2 containing 10% FBS, 2 ng/ml VEGF, and penicillin/streptomycin. After overnight incubation at 37° C. under 5% $CO_2$, a culture supernatant was harvested, and reacted with a nitric oxide (NO) Detection Kit (Intron Biotechnology). Absorbance at 540 nm was detected using a VersaMax Microplate Reader (Molecular Devices) after a 10 minute incubation at room temperature.

Example 5

Epigenetic and Genetic Profile Analysis of Induced Vascular Endothelial Cells of the Present Invention 5-1. Bisulfite Genomic Sequencing To examine whether the induced vascular endothelial cells (iECs) of the present invention acquired vascular endothelium-like epigenetic reprogramming, a DNA methylation status was analyzed by bisulfite genome sequencing.

In particular, total DNA was isolated using the G-spin Total DNA Extraction Kit (Intron Biotechnology). The Epi-Tect Bisulfite Kit (Qiagen) was used for bisulfate treatment. RT-PCR was conducted according to the method of Example 4-1. PCR products were cloned into the pCR™2.1 vector (Invitrogen). Randomly selected clones were sequenced using M13 forward and reverse primers.

As a result, it was confirmed that cytosine guanine dinucleotides (CpG) in the promoter regions of VE-cadherin and Tie2 in the induced vascular endothelial cells of the present invention were demethylated as in the primary ECs or MS1, whereas they were hypermethylated in mock-infected SFBs (FIG. 20).

5-2. Microarray Analysis

To examine genetic profiles of induced vascular endothelial cells (iECs) of the present invention, microarray analysis was conducted.

In particular, mouse genome-wide gene expression analyses were performed using the Affymetrix GeneChip Mouse Gene 1.0 ST Array. Total RNA was extracted using the RNeasy Mini Kit (Qiagen). Microarray analyses were repeated twice or three times, in accordance with the standard Affymetrix Genechip protocol. Data were analyzed using the GeneSpring GX 7.3 (Agilent). Differential gene expression was determined by combining a statistically significant value (P<0.05) and a threshold value (2 fold). Genes differentially expressed between SFBs and lung ECs, or SFBs and MS-1 were selected for analyses. Unsupervised hierarchical clustering was performed using a standard correlation.

As a result, when global gene expression profiles were compared, the induced vascular endothelial cells of the present invention were clustered similarly to the primary vascular endothelial cells (primary ECs) from mouse lungs and MS1, but were distinct from original SFBs or mock-infected SFBs (FIG. 21).

In particular, the expression of vascular endothelial specific genes was very much increased in the induced vascular endothelial cells (FIG. 22). Further, it was confirmed that the induced vascular endothelial cells were not exactly the same as, but were closely related with the primary ECs and MS1 in prespecified gene ontology analyses for vascular endothelial features such as EC development Interestingly, the induced vascular endothelial cells of the present invention well expressed, at gene level, the other six factors, except for 5F, among 11 selected factors of Example 1-1, although they were not transduced by lentivirus (FIG. 28). This suggests that 11 factors that are key regulators of vascular endothelial development also play a pivotal role in vascular endothelial reprogramming, and this vascular endothelial "transcriptional network" is organized by 5F transduction.

Example 6

Transdifferentiation into Vascular Endothelial Cells Using Three ETS Members

While the present inventors were performing our study, Ginsberg and his colleagues reported that human amniotic cells could be converted into vascular endothelial cells by overexpression of three ETS family members, Er71 (=Etv2), Erg, and FLi1.

In particular, Ginsberg et al. focused only on the ETS family, and selected three members, although the reason they chose those factors among more than 20 ETS family paralogs was not clearly described. After they tried to reprogram various adult and fetal nonvascular cells to vascular endothelial cells, only amniotic cells could be successfully converted. Given that various factors besides the ETS family are involved in vascular endothelial development, this is not surprising.

The present inventors tested whether the combination of Er71, Erg, and Fli1 could activate vascular endothelial programming of mouse adult differentiated fibroblasts. A clear vascular endothelial morphologic change to a cobblestone appearance was not observed after the transduction of Er71/Erg/Fli into SFBs (FIG. 29a). In addition, only 0.3% of SFBs infected with Er71/Erg/Fli was transformed to Tie2-GFP⁺ cells (FIG. 29b), which was not better than Er71 single transduction (0.4%) (FIG. 29c).

From this data, it can be confirmed that the three ETS factors are not sufficient to convert adult differentiated fibroblasts into vascular endothelial cells. In fact, it can be confirmed that Erg and Fli1 significantly decreased the conversion rate when each of them was included in the infection combinations (FIGS. 3, 4, and 7a).

Example 7

Investigation of Pluripotency of Induced Vascular Endothelial Cells of the Present Invention To investigate whether pluripotency was induced after conversion of the vascular endothelial cells of the present invention, 5F was transduced into SFBs isolated from Oct4 promoter-driven GFP expressing mice (C57BL/6×CBA background, Jackson Laboratory) or Nanog promoter-driven GFP expressing mice (12954/Sv, C57BL/6, DBA/2 mixed background, RIKEN).

As a result, it can be confirmed that, although Tie2 expression was successfully induced, Oct4-GFP (FIG. 30) or Nanog-GFP (FIG. 31) was not detected, demonstrating that the induced vascular endothelial cells of the present invention were not involved in activation of pluripotency, as a characteristic of stem cells.

Example 8

Investigation of In Vivo Ischemic Disease Treatment Effect of Induced Vascular Endothelial Cells of the Present Invention To investigate whether the induced vascular endothelial cells of the present invention induced angiogenesis in vivo and, accordingly, provided an ischemic disease treatment effect, lower limb ischemic animal models were used.

In particular, target cells, i.e., SFBs, iECs, vP ECs, and MS1, were respectively transduced with lenti-GFP virus. 2 days later, GFP-labeled cells were harvested. $5 \times 10^5$ cells were resuspended in 50 µl of PBS. 8 week old male athymic nude mice were anesthetized, and left femoral arteries were surgically ligated. Cells were injected into 2 sites of the left thigh. Next, a hindlimb surface blood flow of each mouse was serially measured using a laser Doppler blood perfusion imager (LDPI, Moor Instrument) on postoperative days 0, 3, 7, and 14. On day 14, TRITC-conjugated BS1 lectin was injected into a left ventricle. 30 minutes later, mice were euthanized, and perfusion fixation was done with 4% formalin. After overnight fixation with immersion in 10% formalin, thigh muscles were harvested and embedded in paraffin wax. Multiple 10-µm-thick slices were prepared. For analysis of capillary density, tissue sections were stained with DAPI. For detection of the implanted cells, tissue sections were stained with Alexa Fluor 488-conjugated rabbit anti-GFP (1:200, Invitrogen) and DAPI. Stained slides were examined by an LSM 710 fluorescence microscope (ZEISS).

All data are presented as mean±standard deviation. Student's t-test or one-way analysis of variance (ANOVA) was performed for intergroup comparisons. A repeated-measures ANOVA was used to analyze the serial data of the mouse hindlimb ischemia model. SPSS version 19.0 (IBM) was used for analysis, and at least $P<0.05$ was considered statistically significant.

As a result, it was confirmed that, like lung ECs or MS1, implantation of the induced vascular endothelial cells salvaged ischemic limbs and enhanced limb perfusion recovery (FIG. 32). In addition, it was confirmed that ischemic limbs of iEC-implanted mice showed higher capillary density compared with mock-SFBs (FIGS. 33 and 34) and iECs double positive for GFP and BS1 lectin were found in the injection sites (FIG. 35).

From this data, it can be confirmed that the induced vascular endothelial cells of the present invention induces angiogenesis in vivo and, accordingly, have an ischemic blood vessel disease treatment effect.

Example 9

Selection of Factors for Inducing Transdifferentiation of Human Adult Fibroblasts into Vascular Endothelial Cells As shown in Examples 1 to 8, mouse adult skin fibroblasts were transduced with Foxo1, Er71, Klf2, Tal1, and Lmo2. As a result, it was confirmed that transdifferentiation of mouse adult skin fibroblasts into vascular endothelial cells can be induced by the factors. This example was performed to select the optimal factor to induce transdifferentiation of human adult fibroblasts into vascular endothelial cells. Experiments were performed as follows.

9-1. Isolation of Human Adult Fibroblasts

Human dermal fibroblasts (HDFs) to be differentiation-induced into vascular endothelial cells were separated from human adult fibroblasts.

In particular, a skin fragment of donated human tissue was peel off using surgical scissors. After the removal of fat, the dermis separated from the epidermis by a pair of sterile forceps. The dermis was washed three times with phosphate-buffered saline (PBS), and sliced into 4 to 5 pieces. The pieces were incubated in DMEM (Gibco) with 0.1% collagenase (Gibco) on a 35 mm petri-dish (SPL) for 1.5 hours at 37° C. under 5% $CO_2$. Next, tissue fragments were rinsed three times with PBS, and treated with 0.25% trypsin (Gibco) for 20 min. Cells were collected by centrifugation (1300 rpm for 7 min at 4° C.), resuspended in DMEM containing 10% FBS (Gibco), penicillin/streptomycin (Gibco), L-Glutamine (Gibco), and sodium pyruvate (Gibco), and seeded on 0.1% gelatin-coated 6 well plates (Nunc).

9-2. Infection of Human Adult Fibroblasts with Lentivirus

The target cells confirmed in Example 9-1 were cultured in DMEM with a lentivirus expressing 11 factors selected in Example 2 and 10 mg/ml of Polybrene. By such culturing, the cells were infected with the lentivirus. After allowing the infection for 24 hours, the medium containing the lentivirus was replaced with fresh DMEM containing 10% FBS and penicillin/streptomycin. After 24 hours, the medium was replaced with EBM-2 containing 10% FBS and penicillin/streptomycin again. 12 days after the viral infection, cells were harvested and subjected to a FACS analysis using the same method as in Example 1-2.

Example 10

Selection of Three Factors Suitable for Inducing Transdifferentiation of Human Adult Fibroblasts into Vascular Endothelial Cells To investigate whether the five factors confirmed in Example 2 also induced transdifferentiation of human adult fibroblasts into vascular endothelial cells, human adult skin fibroblasts were transduced with lentivirus expressing each factor. Cells simultaneously expressing VE-cadherin and PECAM-1, as markers most specific to human vascular endothelial cells, were analyzed using FACS. Results are illustrated in FIG. 36.

As a result, when Er71 was excluded (5F-Er71) and Klf2 was excluded (5F-Klf2), the proportions of vascular endothelial cells expressing simultaneously VE-cadherin and PECAM-1, as the most specific markers of human vascular endothelial cells, were decreased, compared to the human adult fibroblasts transduced with all of the five factors (5F).

However, it was confirmed that, when three factors (3F), Er71, Klf2, and Tal1, except for Foxo1 and Lmo2, were transduced, the proportion of vascular endothelial cells remarkably increased, compared to the case in which transduction with all of the five factors was performed (5F).

Accordingly, transduction with another factor, in addition to the three factors (Er71, Klf2, and Tal1), was additionally performed (3F+Foxc2, 3F+Gata2, 3F+Fli1, 3F+Erg, 3F+Ets1, 3F+Elf1, 3F+Foxf1, and 3F+Mef2c), transduction was performed without any one of the three factors (2F (EK), 2F (ET), and 2F (KT)), or each of Er71, Klf2, and Tal1 was exclusively used for transduction (1F (Er71), 1F (Klf2), 1F (Tal1)). As results, it was confirmed, in these cases, the proportions of vascular endothelial cells were decreased, compared to the case of 3F. From this data, it can be confirmed that the combination of the three factors is the most effective and essential combination to induce differentiation of human adult skin fibroblasts into vascular endothelial cells. Such transdifferentiated cells were named human induced vascular endothelial cell.

Example 11

Analysis of Characteristics of Induced Human Vascular Endothelial Cells of the Present Invention After transduction with 3F was performed, endothelial functions of resultant induced human vascular endothelial cells were analyzed.

11-1. Induction of Differentiation of Human Fibroblasts (HDFs) into Vascular Endothelial Cells To reconfirm whether the combination of the three differentiation induction factors (Er71, Klf2, and Tal1: 3F) confirmed in Example 10 induced transdifferentiation of human adult fibroblasts into vascular endothelial cells, human adult fibroblasts were transduced with 3F. As a result, it was confirmed that the transduced cells had a morphology similar to vascular endothelial cells (FIG. 37).

11-2. Immunofluorescence Staining

The induced human vascular endothelial cells of the present invention show a DiI-acLDL uptake ability, as a characteristic of endothelial cells (FIG. 38).

Experiments were performed as in Example 4-2. To investigate DiI-Ac-LDL uptake, cells were reacted under conditions of 10 μg/ml of DiI-Ac-LDL (Invitrogen), 37° C., and 5% $CO_2$ for 12 hours and then stained with DAPI. DiI-Ac-LDL uptake was imaged using an LSM 710 fluorescence microscope.

11-3. Matrigel Tube Formation and NO Generation

In addition, it was confirmed that the induced human vascular endothelial cells (3F-hiEC) of the present invention were formed into capillary tubes on Matrigel, similarly to HUVEC cells (FIG. 39) and can produce nitric oxide (NO), as an important factor for the functionality of blood vessels, in an amount equal to that produced by HUVEC and GEAEC cells (FIG. 40).

A particular experimental method was the same as in Example 4-3. As comparison subjects, human umbilical vein endothelial cells (HUVEC) and human gastric epiploic artery endothelial cells (GEACE) were used.

11-4. Observation by Means of Scanning Electron Microscopy (SEM)

In addition, the induced human vascular endothelial cells (3F-hiEC) of the present invention were observed by means of scanning electron microscopy. Results are illustrated in FIG. 41.

As a result, it was confirmed that 3F-hiEC had a morphology similar to HUVEC and GEACE, as vascular endothelial cells.

The aforementioned description of the present invention is provided by way of example and those skilled in the art will understood that the present invention can be easily changed or modified into other specified forms without change or modification of the technical spirit or essential characteristics of the present invention. Therefore, it should be understood that the aforementioned examples are only provided by way of example and not provided to limit the present invention.

The invention claimed is:

1. A method of preparing mouse vascular endothelial cells by transdifferentiating mouse adult fibroblasts, comprising transducing the mouse adult fibroblasts in vitro/ex vivo with one or more expression vector(s) comprising mouse Foxo1, Er71 and Klf2 genes in operable linkage to expression control elements, wherein the expression of each of Foxo1, Er71 and Klf2 induces the transdifferentiation of the mouse adult fibroblasts to mouse vascular endothelial cells.

2. The method according to claim 1, wherein the expression vector further comprise Tal1 gene.

3. The method according to claim 1, wherein the expression vector further comprise Tal1 and LMO gene.

4. A method of preparing human vascular endothelial cells by transdifferentiating human adult fibroblasts, comprising transducing the human adult fibroblasts in vitro/ex vivo with one or more expression vector(s) comprising human Er71, Klf2 and Tal1 genes in operable linkage to expression control elements, wherein the expression of each of Er71, Klf2 and Tal1 induces the transdifferentiation of the human adult fibroblasts to human vascular endothelial cells.

5. A method of treating an ischemic disease comprising administering directly to the site of ischemic injury of a subject in need thereof an effective amount of the mouse or human vascular endothelial cells prepared by the method of any of claims 1 to 4.

6. The method according to claim 5, wherein the ischemic disease is selected from the group consisting of ischemic heart disease, ischemic cerebrovascular disease and ischemic limb disease.

7. The method according to claim 6, wherein the ischemic heart disease is selected from the group consisting of coronary artery disease, angina, myocardial infarct, congestive heart failure, chronic heart failure, cardiomyopathy, and myocardial infarction.

* * * * *